(12) United States Patent
Frohlich

(10) Patent No.: US 11,589,806 B2
(45) Date of Patent: Feb. 28, 2023

(54) FEEDBACK BRAIN STIMULATION TO ENHANCE SLEEP SPINDLES, MODULATE MEMORY AND COGNITIVE FUNCTION, AND TREAT PSYCHIATRIC AND NEUROLOGICAL SYMPTOMS

(71) Applicant: The University of North Carolina at Chapel Hill, Chapel Hill, NC (US)

(72) Inventor: Flavio Frohlich, Chapel Hill, NC (US)

(73) Assignee: THE UNIVERSITY OF NORTH CAROLINA AT CHAPEL HILL, Chapel Hill, NC (US)

(*) Notice: Subject to any disclaimer, the term of this patent is extended or adjusted under 35 U.S.C. 154(b) by 523 days.

(21) Appl. No.: 15/571,551

(22) PCT Filed: May 5, 2016

(86) PCT No.: PCT/US2016/031013
§ 371 (c)(1),
(2) Date: Nov. 3, 2017

(87) PCT Pub. No.: WO2016/179407
PCT Pub. Date: Nov. 10, 2016

(65) Prior Publication Data
US 2018/0140249 A1    May 24, 2018

Related U.S. Application Data

(60) Provisional application No. 62/158,267, filed on May 7, 2015.

(51) Int. Cl.
*A61B 5/00* (2006.01)
*A61N 1/36* (2006.01)
(Continued)

(52) U.S. Cl.
CPC ............ *A61B 5/4812* (2013.01); *A61B 5/375* (2021.01); *A61B 5/7253* (2013.01);
(Continued)

(58) Field of Classification Search
None
See application file for complete search history.

(56) References Cited

U.S. PATENT DOCUMENTS

| 2008/0319505 A1* | 12/2008 | Boyden .............. A61N 1/36021 607/45 |
| 2012/0053508 A1* | 3/2012 | Wu ..................... A61B 5/04001 604/20 |

(Continued)

FOREIGN PATENT DOCUMENTS

WO    WO 2015/069632 A1    5/2015

OTHER PUBLICATIONS

Kuwahara, H., Higashi, H., Mizuki, Y., Matsunari, S., Tanaka, M., & Inanaga, K. (1988). Automatic real-time analysis of human sleep stages by an interval histogram method. Electroencephalography and Clinical Neurophysiology, 70(3), 220-229. doi: 10.1016/0013-4694(88)90082-x (Year: 1988).*

(Continued)

*Primary Examiner* — Etsub D Berhanu
(74) *Attorney, Agent, or Firm* — J. Clinton Wimbish; Nexsen Pruet, PLLC

(57) ABSTRACT

The present invention relates to methods for modulating bursts of oscillatory brain activity, such as sleep spindles, in a subject. The invention further relates to methods of improving memory or cognitive function in a subject and method of modulating or enhancing the frequency of occurrence, structure, amplitude, and/or synchronization of sleep spindles in a subject by detecting a burst of oscillatory brain (Continued)

activity in the subject and passing an oscillating current through the skull of the subject.

27 Claims, 9 Drawing Sheets

(51) Int. Cl.
　　*A61N 1/04*　　　(2006.01)
　　*A61B 5/375*　　(2021.01)
　　*A61B 5/389*　　(2021.01)
　　*A61B 5/398*　　(2021.01)

(52) U.S. Cl.
　　CPC .......... *A61B 5/7282* (2013.01); *A61N 1/0456* (2013.01); *A61N 1/0484* (2013.01); *A61N 1/36025* (2013.01); *A61B 5/389* (2021.01); *A61B 5/398* (2021.01)

(56) References Cited

U.S. PATENT DOCUMENTS

| | | | | |
|---|---|---|---|---|
| 2012/0296390 | A1* | 11/2012 | Nakashima | A61N 1/36025 607/45 |
| 2015/0066104 | A1* | 3/2015 | Wingeier | A61B 5/4836 607/45 |
| 2015/0343196 | A1* | 12/2015 | Vasapollo | A61N 1/048 607/45 |
| 2016/0256105 | A1* | 9/2016 | Boyle | A61B 3/112 |
| 2017/0196474 | A1* | 7/2017 | Garcia Molina | A61B 5/048 |
| 2018/0008827 | A1* | 1/2018 | Dolev | A61B 5/369 |
| 2018/0028813 | A1* | 2/2018 | Miller | A61N 1/37247 |

OTHER PUBLICATIONS

Huupponen, E., Varri, A., Himanen, S.-L., Hasan, J., Lehtokangas, M., & Saarinen, J. (2000). Optimization of sigma amplitude threshold in sleep spindle detection. Journal of Sleep Research, 9(4), 327-334. doi: 10.1046/j.1365-2869.2000.00220.x (Year: 2000).*

Ali, M. M., Sellers, K. K., & Frohlich, F. (2013). Transcranial Alternating Current Stimulation Modulates Large-Scale Cortical Network Activity by Network Resonance. Journal of Neuroscience, 33(27), 11262-11275. doi: 10.1523/jneurosci.5867-12.2013 (Year: 2013).*
Zaehle, T., Rach, S., & Herrmann, C. S. (2010). Transcranial Alternating Current Stimulation Enhances Individual Alpha Activity in Human EEG. PLoS ONE, 5(11). doi:10.1371/journal.pone. 0013766 (Year: 2010).*
Boyle et al. EEG Feedback-Controlled Transcranial Alternating Current Stimulation. 6th Annual International IEEE EMBS Conference on Neural Engineering. (Year: 2013).*
Frohlich. Endogenous and exogenous electric fields electric fields as modifiers of brain activity: rational design of noninvasive brain stimulation with transcranial alternating current stimulation. (Year: 2014).*
Marshall et al. Boosting slow oscillations during sleep potentiates memory. Nature, Dec. 2006. (Year: 2006).*
Marshall et al. Transcranial Direct Current Stimulation during Sleep Improves Declarative Memory. The Journal of Neuroscience, Nov. 3, 2004, 24(44) 9985-9992. (Year: 2004).*
Fogel et al. The function of the sleep spindle: A physiological index of intelligence and a mechanism for sleep-dependent memory consolidation. Neuroscience and Biobehavioral Reviews 35 (2011) 1154-1165. (Year: 2011).*
Cox et al. Local sleep spindle modulations in relation to specific memory cues. NeuroImage 99 (2014) 103-110. (Year: 2014).*
Notification Concerning Transmittal of International Preliminary Report on Patentability corresponding to International Application No. PCT/US2016/031013 dated Nov. 16, 2017.
Keshavan et al. "Sleep Correlates of Cognition in Early Course Psychotic Disorders", *Schizophr Res.* 131(1-3):231-234 (2011).
Bazanova O.M. Sovremennaya interpretatsiya alfa-aktivnosti EEGI. Mezhdunarodny nevrologicheski y zhurnal, 2011, 8 ( 46).
Poehlmann et al. "Risk and Resilience in Preterm Children at Age 6", *Dev Psychopathol.* 27(3):843-858 (2015.
Notification of Transmittal of the International Search Report and the Written Opinion of the International Searching Authority, or the Declaration corresponding to International Application No. PCT/US2016/031013 dated Aug. 18, 2016.

* cited by examiner

FIGS. 2A-2E
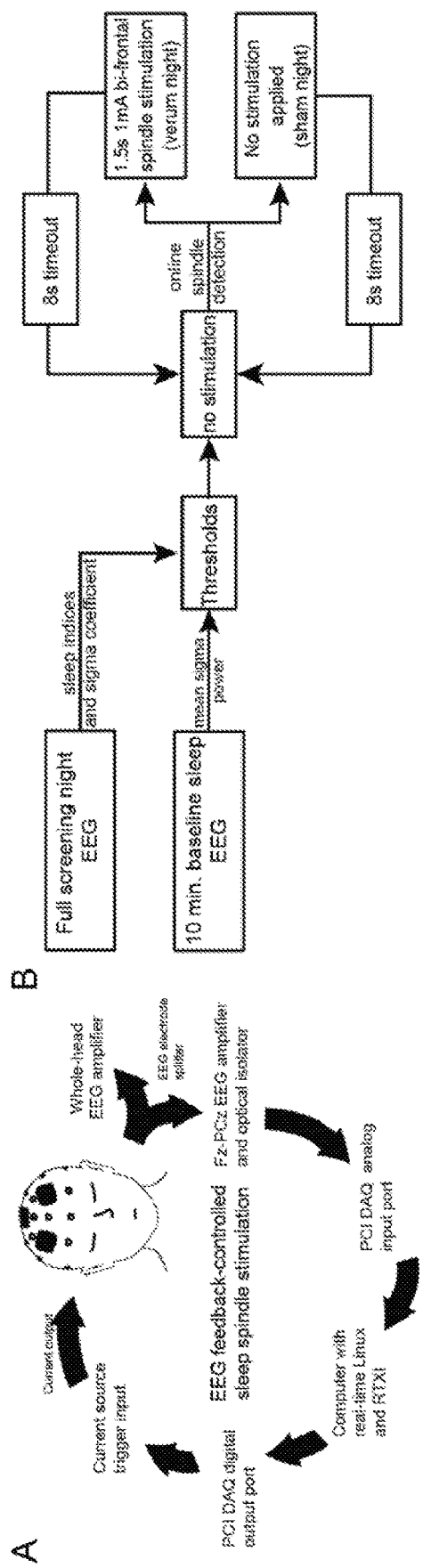
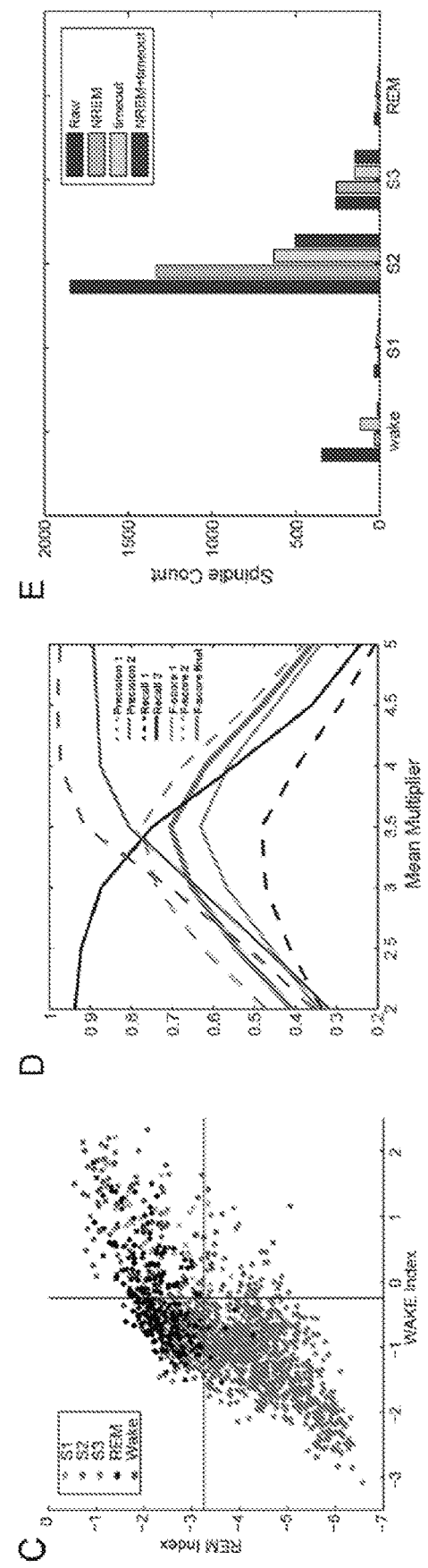

FIGS. 6A-6C
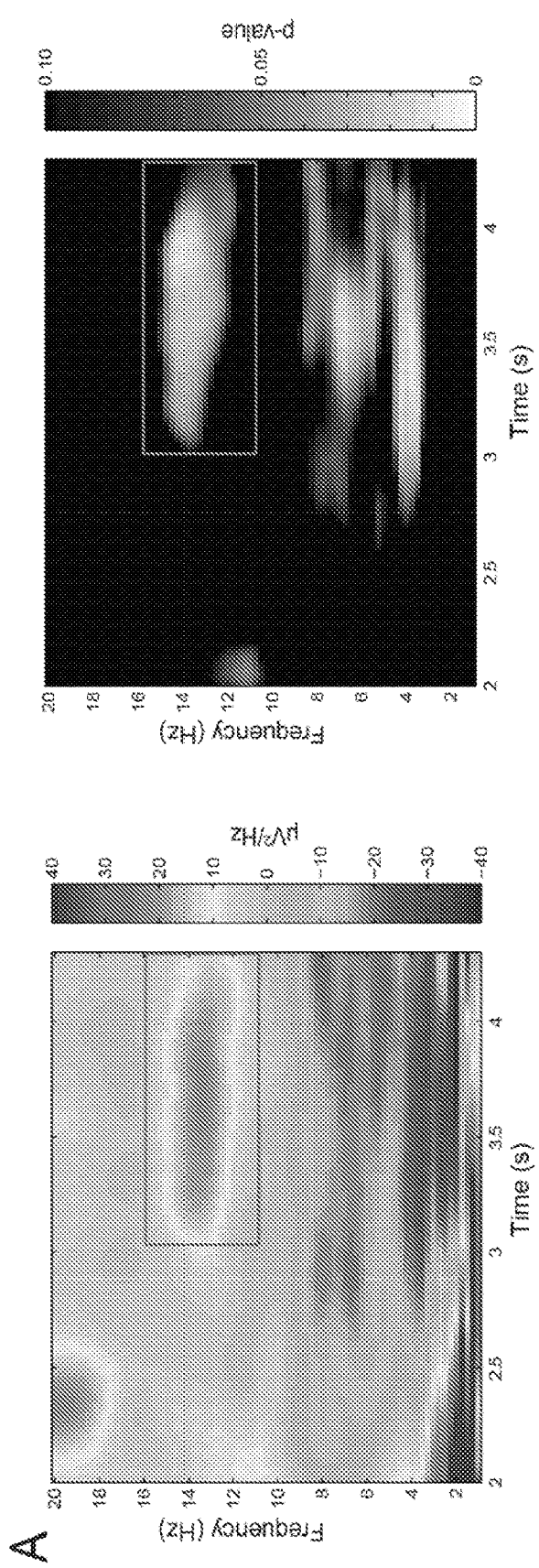
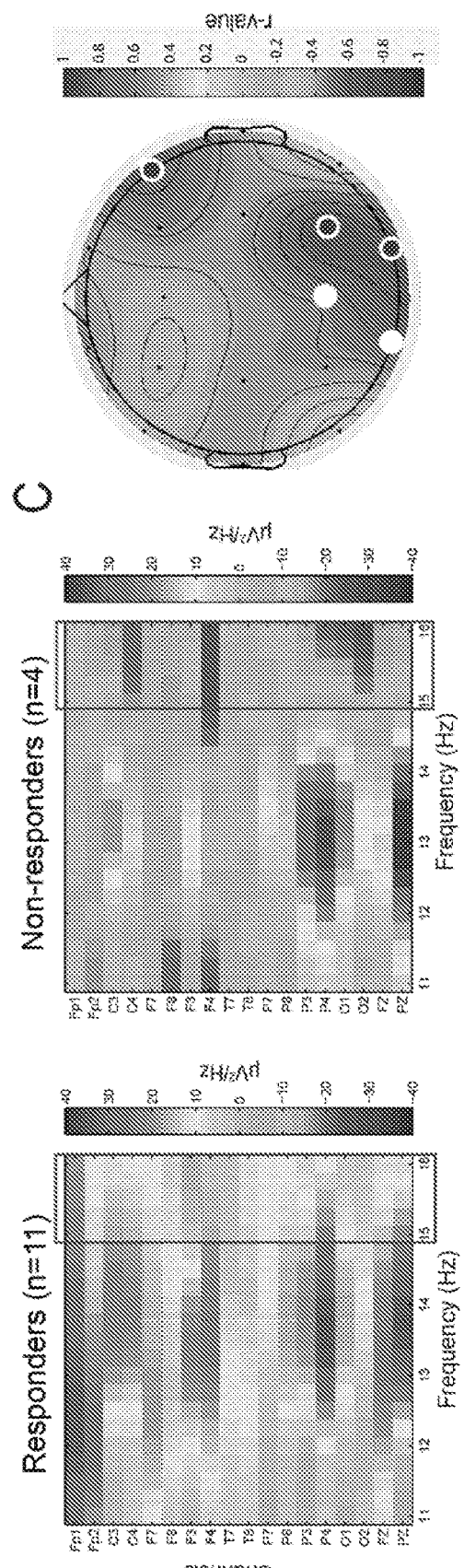

US 11,589,806 B2

FEEDBACK BRAIN STIMULATION TO ENHANCE SLEEP SPINDLES, MODULATE MEMORY AND COGNITIVE FUNCTION, AND TREAT PSYCHIATRIC AND NEUROLOGICAL SYMPTOMS

STATEMENT OF PRIORITY

This application is a 35 U.S.C. § 371 national phase application of PCT Application PCT/US2016/031013 filed May 5, 2016, which claims the benefit of U.S. Provisional Application Ser. No. 62/158,267, filed May 7, 2015, the entire contents of each, of which e incorporated by reference herein.

STATEMENT OF GOVERNMENT SUPPORT

This invention was made with government support under Grant No. MH101547 awarded by National Institutes of Health. The government has certain rights to this invention.

FIELD OF THE INVENTION

The present invention relates to methods for modulating bursts of oscillatory brain activity, such as sleep spindles, in a subject. The invention further relates to methods of improving memory or cognitive function in a subject and method of modulating or enhancing the frequency of occurrence, structure, amplitude, and/or synchronization of sleep spindles in a subject by detecting a burst of oscillatory brain activity in the subject and passing an oscillating current through the skull of the subject.

BACKGROUND

Oscillatory patterns are fundamental to the organization of thalamo-cortical activity and are conserved across species (Buzsaki et al., *Neuron* 80:751 (2013); Buzsaki et al., *Science* 304:1926 (2004)). The presence of oscillations at different frequencies is dynamically regulated as a function of overall behavioral state and moment-to-moment fluctuations in cognitive demands (Buzsaki et al., *Neuron* 80:751 (2013); Buzsaki et al., *Science* 304:1926 (2004); Harris et al., *Nat. Rev. Neurosci.* 12:509 (2011); Lee et al., *Neuron* 76:209 (2012)). The transient occurrence of pronounced rhythmic activity is commonly observed in recordings of cortical network dynamics. However, the causal role of the dynamic occurrence of brain oscillations remains poorly understood. Most prominently, sleep spindles are transient electroencephalograph (EEG) oscillations between 11 and 16 Hz (De Gennaro et al., *Sleep Med. Rev.* 7:423 (2003); Warby et al., *Nat. Methods* 11:385 (2014)). The functional role of sleep spindles in cognitive processes has been hypothesized but not yet been directly demonstrated (Fogel et al., *Neurosci. Biobehav. Rev.* 35:1154 (2011); Rasch et al., *Physiol. Rev.* 93:681 (2013)). Besides the issue that the majority of previous studies on the role of sleep spindles are based on correlations between sleep spindles and memory consolidation, the few studies that manipulated sleep using tones, electrical stimulation or pharmacology enhanced sleep spindles as a side effect of enhancing slow oscillations/slow wave sleep (Del Felice et al., *Brain Stimulation* 8:567 (2015); Marshall et al., *Nature* 444:610 (2006); Mednick et al., *J. Neurosci.* 33:4494 (2013); Ngo et al., *Neuron* 78:545 (2013); Westerberg et al., *Neurobiol. Aging* 36:2577 (2015)). This fundamental gap in our understanding of these thalamo-cortical oscillations is the result of the lack of a tool to monitor and selectively enhance transient epochs of oscillatory activity in real-time in humans. Transcranial alternating current stimulation (tACS) applies a weak electrical current to the scalp and recent evidence demonstrates that tACS is capable of inducing frequency-specific effects on brain dynamics (Boyle et al., In Neural Engineering (NER), 2013 6th International IEEE/EMBS Conference on. (IEEE), pp. 140-143 (2013); Helfrich et al., *Curr. Biol.* 24:333 (2014); Schmidt et al., *Brain Stimul.* 7:878 (2014); Vossen et al., *Brain Stimul.* 8:499 (2015); Herrmann et al., *Int. J. Psychophysiol.* pii: S0167-8760(15)00033-1. doi: 10.1016/j.ijpsycho.2015.02.003. (2015); Herrmann et al., *Front. Hum. Neurosci.* 7:279 (2013)) and can be used to identify the functional role of brain oscillations in cognition (Herrmann et al., *Front. Hum. Neurosci.* 7:279 (2013); Fröhlich, *Dialogues Clin. Neurosci.* 16:93 (2014); Lustenberger et al., *Cortex* 67:74 (2015); Santarnecchi et al., *Curr. Biol.* 23:1449 (2013)). Yet no approach to selectively target transient oscillations has been described.

A need exists for effective and specific modulation of brain oscillations such as sleep spindles.

SUMMARY OF EMBODIMENTS OF THE INVENTION

Animal studies and computational models showed that the effectiveness of transcranial electrical stimulation (tES) relies on the internal network dynamics; therefore stimulation paradigms that resemble the temporal structure of endogenous activity patterns are the most effective (Schmidt et al., *Brain Stimul.* 7:878 (2014); Ali et al., *J. Neurosci.* 33:11262 (2013); Fröhlich et al., *Neuron* 67:129 (2010); Ozen et al., *J. Neurosci.* 30:11476 (2010); Reato et al., *PLoS Comput. Biol.* 9:e1002898 (2013); Brittain et al., *Curr. Biol.* 23:436 (2013)). Based on these findings, it was hypothesized that real-time detection of transient oscillations that trigger short epochs of transcranial alternating current stimulation (tACS) resembling the targeted endogenous oscillation provides a mean to boost transient oscillations. Sleep spindles represent the ideal target oscillation to apply this approach for several reasons: (1) Sleep spindles are clearly defined and dominant distinct oscillations during non-rapid eye movement (NREM) sleep that can be targeted in real-time; (2) So far, no approach was described that enhanced sleep spindle activity without increasing other sleep oscillations or the time spent in specific sleep stages (Marshall et al., *Nature* 444:610 (2006); Mednick et al., *J. Neurosci.* 33:4494 (2013); Ngo et al., *Neuron* 78:545 (2013)); (3) Their proposed role in cognitive processes such as memory consolidation still needs to be demonstrated; and (4) Several psychiatric and neurologic disorders are hallmarked by sleep spindle deficits, such as Alzheimer's disease (Rauchs et al., *Neuroreport* 19:1159 (2008)), autism (Limoges et al., *Brain* 128:1049 (2005)) and schizophrenia (Ferrarelli, *Curr. Sleep Med. Rep.* 1:150 (2015); Ferrarelli et al., *Am. J. Psychiatry* 164:483 (2007); Ferrarelli et al., *Am. J. Psychiatry* 167:1339 (2010); Manoach et al., *J. Psychiatr. Res.* 44:112 (2010); Wamsley et al., *Biol. Psychiatry* 71:154 (2012)). An EEG feedback-controlled approach was used that restricts the application of tACS (FB-tACS) in the spindle frequency range to when a sleep spindle during NREM sleep is detected and therefore only enhances neuronal networks when spindle activity is prevailing. This tool was used to ask the question if sleep spindles play a causal role in memory consolidation. This is a question of significant translational relevance given the number of neurological and psychiatric conditions associated with memory impairment (Manoach et al., *J. Psychiatr. Res.* 44:112 (2010); Wamsley et al., *Biol. Psychiatry* 71:154 (2012)). It was found that spindle FB-tACS caused an enhancement of cortical synchronization in the spindle frequency range that intensified the spindling process and improved memory consolidation.

The present invention is based on the development of real-time feedback techniques for modulating bursts of oscillatory brain activity, such as sleep spindles, in a subject. The invention is further based on the ability of real-time feedback to improve memory or cognitive function in a subject and to treat a psychiatric or neurological symptom associated with impairment of sleep spindle oscillation and/or impairment of cognitive function in a subject.

Thus, one aspect of the invention relates to a method of improving memory or cognitive function in a subject, the method comprising: a) detecting a burst of oscillatory brain activity in the subject; and b) passing an oscillating current through the skull of the subject; thereby improving memory or cognitive function in the subject.

Another aspect of the invention relates to a method of modulating or enhancing the frequency of occurrence, structure, amplitude, and/or synchronization of sleep spindles in a subject, the method comprising: a) detecting a burst of oscillatory brain activity in the subject; and b) passing an oscillating current through the skull of the subject; thereby modulating or enhancing the frequency of occurrence, structure, amplitude, and/or synchronization of sleep spindles in the subject.

A further aspect of the invention relates to a method of treating a psychiatric or neurological symptom associated with impairment of sleep spindle oscillation and/or impairment of cognitive function in a subject in need thereof, the method comprising: a) detecting a burst of oscillatory brain activity in the subject; and b) passing an oscillating current through the skull of the subject; thereby treating the psychiatric or neurological symptom associated with sleep spindles in the subject.

These and other aspects of the invention are set forth in more detail in the description of the invention below.

BRIEF DESCRIPTION OF THE DRAWINGS

FIGS. 2A-2E show a novel feedback control system for real-time detection and stimulation of sleep spindles. (A) Graphical representation of feedback control system component inter-connection. (B) Algorithm flow chart outlining major steps in the procedures implemented by the control system. (C) Scatter plot used to set REM index and wake index thresholds, shown here for a representative participant. Colors represent 20 s epoch classifications by professional sleep stager; REM and wake indices determine the position of each epoch within the plane. Horizontal and vertical black lines represent, respectively, the REM and wake index thresholds determined by the experimenter to maximally detect S2 and S3 epochs with few false positives. (D) Sigma threshold multiplier performance assessment plots, relative to an offline spindle detection algorithm developed by Ferrarelli et al., *Am. J Psychiatry* 164:483 (2007). F-scores (green, red), precision (blue), and recall (black) are shown as a function of mean sigma amplitude multiplier for a representative participant. Mean multiplier with highest final F-score (red, 3.5 in this example) was chosen. (E) Bar plot showing number of spindles detected, grouped by sleep stage (as determined by expert scorer) for a representative participant during a screening night. Each level of algorithmic refinement (raw spindles as determined by sigma activity, raw spindles that also meet NREM detection criteria, raw spindles adhering to the 6.5 s timeout rule, raw spindles that meet NREM detection and adhere to the 6.5 s timeout rule) is shown as a different color bar for each sleep stage.

FIGS. 6A-6C show FB-tACS increases spindle activity during NREM stage 2 sleep that is related to stimulation-induced motor sequence tapping speed gains. (A) Difference of spectrograms (verum−sham) for longest artifact free interval during NREM stage 2 (N2, 2-4.3 s) and corresponding p-values of a paired t-test between sham and verum condition (p values>0.1 are black, pink rectangles highlight window with increased spindle activity). (B) Detailed analysis of increased spindle activity window during N2 (11-16 Hz, pink window in A). Spectrogram values were averaged over time for the selected time window and plotted for each frequency bin and channel. This analysis was done for responders (n=11, superior speed gain in motor sequence task for verum condition compared to sham) and non-responders separately (n=4). (C) Topographical representation of Pearson correlation coefficients between the spindle activity difference (n=15; pooled for responders and non-responders) for 15-16 Hz (black rectangle in B) with the difference (verum−sham) in overnight speed gain (FIG. 4B). Superior speed gain in verum condition compared to sham is reflected in a negative number as superior speed means reduced response time. Thus, negative correlation coefficients show that more spindle activity increase is related to a more pronounced sleep-dependent response time decrease (speed increase) in the verum condition compared to sham. Electrodes (black dots) that showed a significant correlation (Pearson) are marked with grey dots ($p<0.05$) and electrodes that showed a trend-level with white dots ($p\geq 0.05$ and $p<0.1$). The size of the cluster (4 neighboring electrodes with grey and white dots) was significant after performing a supra-threshold cluster analysis.

DETAILED DESCRIPTION OF THE INVENTION

Figures 1A, 1B:
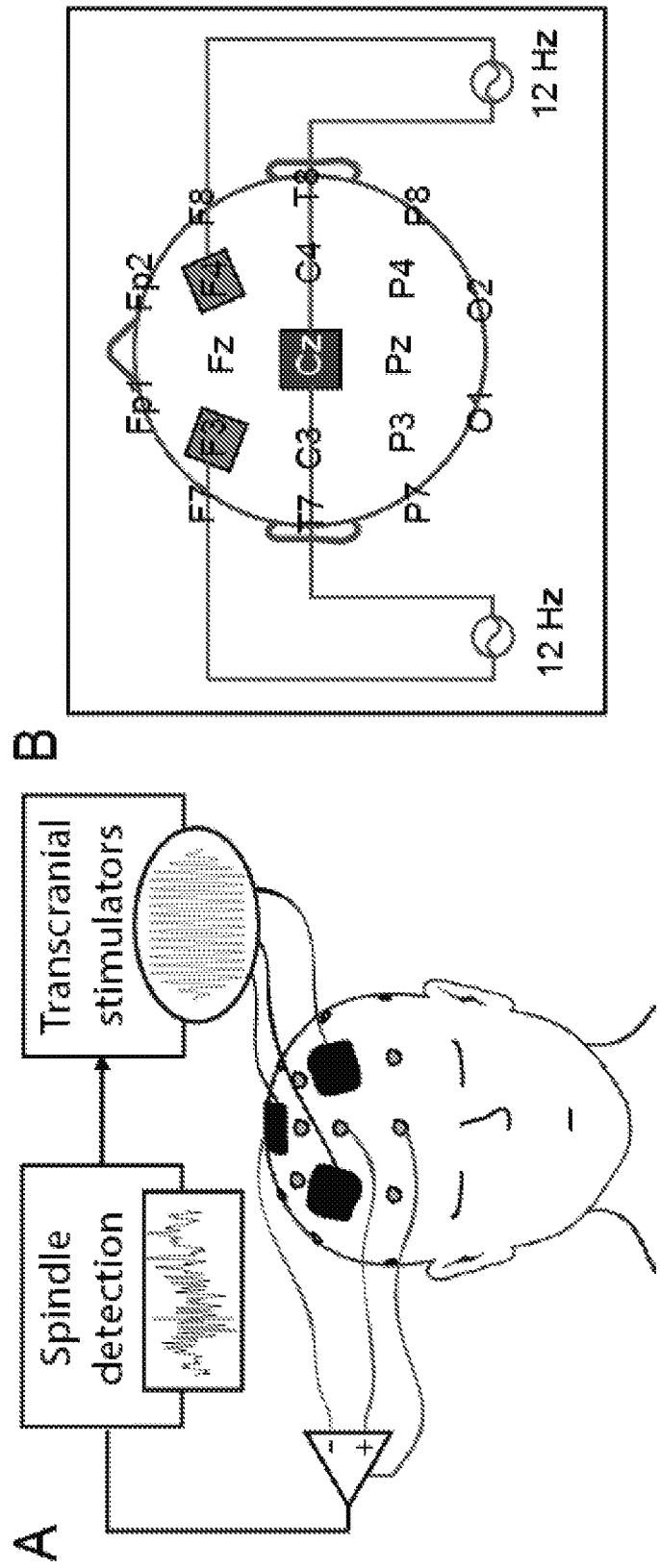
FIGS. 1A-1B show feedback-controlled spindle tACS. (A) Graphical representation of real-time spindle detection and feedback-controlled transcranial current stimulation. (B) Schematic of tACS current source and stimulation electrode configuration; stimulation electrode placement according to International 10-20 locations.

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

It will be understood that when an element or layer is referred to as being "on", "attached to", "connected to", "coupled to", "coupled with" or "contacting" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. It will also be appreciated by those of skill in the art that references to a structure or feature that is disposed "adjacent" another structure or feature may have portions that overlap or underlie the adjacent structure or feature.

As will be appreciated by one skilled in the art, aspects of the present invention may be embodied in hardware and/or software (including firmware, resident software, microcode, etc.). Accordingly, aspects of the present invention may be illustrated and described herein with respect to various combinations of hardware/software referred to as circuits, modules, devices and/or systems. In some embodiments, aspects of the present invention may take the form of a computer program product on a computer-usable or computer-readable medium having computer-usable or computer-readable program code embodied therein.

Any suitable computer-usable or computer-readable media may be used, including, but not limited to, computer-usable or computer-readable media signal media and computer-usable or computer-readable storage media.

In some embodiments, aspects of the present invention take the form of a computer program product on a computer-usable or computer-readable storage medium (e.g., a non-transient computer-usable or computer-readable storage medium) having computer-usable or computer-readable program code embodied in the medium for use by or in connection with an instruction execution system. A computer-usable or computer-readable storage medium may be any tangible medium that can contain and/or store the program for use by or in connection with the instruction execution system, apparatus or device. For example, the computer-usable or computer-readable storage medium may be an electronic, optical, electromagnetic, infrared or semiconductor system, apparatus or device or any suitable combination thereof. Accordingly, in some embodiments, aspects of the present invention are embodied in portable computer diskette, a hard disk, a random access memory (RAM), a read-only memory (ROM), an erasable programmable read-only memory (EPROM or Flash memory), an optical fiber with a repeater, a portable compact disc read-only memory (CD-ROM), an optical storage device, a magnetic storage device or any suitable combination thereof.

In some embodiments, aspects of the present invention take the form of a computer program product on a computer-usable or computer-readable signal medium having computer-usable or computer-readable program code embodied in the medium for use by or in connection with an instruction execution system. A computer-usable or computer-readable signal medium may be any computer-usable or computer-readable medium that is not a computer-usable or computer-readable storage medium and that can communicate, propagate and/or transport a program for use by or in connection with the instruction execution system, apparatus or device. A computer-usable or computer-readable signal medium may comprise a propagated data signal with computer-usable or computer-readable program code embodied therein. For example, the computer-usable or computer-readable signal medium may comprise computer-usable or computer-readable program code embodied in a baseband or carrier wave. The propagated data signal may take any suitable form, including, but not limited to electro-magnetic and optical. The propagated data signal may be communicated, propagated and/or transmitted using any suitable medium, including, but not limited to, wired and wireless communications channels. Accordingly, in some embodiments, aspects of the present invention are embodied in a computer-usable or computer-readable signal medium that is transmitted over a LAN, the Internet, a public telephone switching network, Bluetooth, WLAN or any suitable combination thereof.

Computer program code for carrying out operations for aspects of the present invention may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer (e.g., entirely on an evaluation portal), partly on the user's computer (e.g., partly on an evaluation portal), as a stand-alone software package, partly on the user's computer and partly on a remote computer (e.g., partly on an evaluation portal and partly on an evaluation hub) or entirely on the remote computer or server (e.g., entirely on an evaluation hub). In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

As used herein, the singular forms "a", "an" and "the" are intended to include the plural forms as well, unless the context clearly indicates otherwise.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "adjuvant treatment" refers to a treatment session/regimen in which the administration of one or more oscillating electric currents (OECs) through the skull of a subject modifies the effect(s) of one or more active agents and/or therapies. For example, the administration of one or more OECs through the skull of a subject may enhance the effectiveness of a pharmaceutical agent (by restoring the therapeutic efficacy of a drug to which the subject had previously become habituated, for example). Likewise, the administration of one or more OECs through the skull of a subject may enhance the effectiveness of counseling or psychotherapy. In some embodiments, the administration of one or more OECs through the skull of a subject reduces or eliminates the need for one or more active agents and/or therapies. Adjuvant treatments may be effectuated by administering one or more OECs through the skull of a subject prior to, currently with and/or after administration of one or more active agents and/or therapies.

As used herein, the term "and/or" includes any and all combinations of one or more of the associated listed items.

As used herein, the terms "chronic treatment," "chronically treating" and the like refer to a therapeutic treatment carried out at least once per week (e.g., two or three times per week, daily, etc.) over an extended period of time. Chronic treatment typically lasts at least one to two weeks (and, in some embodiments, at least one to two months), but may last as long as required to achieve and/or maintain therapeutic efficacy for the particular condition or disorder for which the treatment is carried out (i.e., the device may be used periodically throughout the subject's life).

As used herein, the terms "comprise," "comprises," "comprising," "include," "includes" and "including" specify the presence of stated features, integers, steps, operations, elements, and/or components, but do not preclude the presence or addition of one or more other features, integers, steps, operations, elements, components, and/or groups thereof.

As used herein, the term "consists essentially of" (and grammatical variants thereof), as applied to the compositions and methods of the present invention, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to a composition of the present invention would "materially alter" the composition if it increases or decreases the composition's durability by at least 20%.

As used herein, the term "cortical oscillations" refers to rhythmic and/or repetitive neural activity in the cerebral cortex of a subject. Cortical oscillations may manifest as oscillations in the membrane potential of one or more neurons and/or as the rhythmic firing or one or more neurons. In some embodiments, cortical oscillations arise from and are indicative of synchronized neuronal activity within a specific brain region. In some embodiments, cortical oscillations arise from and are indicative of synchronized neuronal activity in two or more brain regions. In some embodiments, cortical oscillations arise from and are indicative of a feedback loop (e.g., a positive feedback loop) between brain regions. For example, cortical oscillations in the alpha frequency band may arise from and be indicative of a feedback loop in the thalamocortical network.

As used herein, the term "burst of oscillatory brain activity" refers to a series of cortical oscillations that occurs within a short amount of time. A burst is defined in this context as the transient occurrence of an oscillatory activity signature which can last anywhere from 100 milliseconds to few seconds. Typically, each such burst contains at least three consecutive oscillation cycles which enables the determination as a burst of an oscillation. Therefore, the minimal and typical duration of bursts of oscillations depends on the oscillation frequency.

As used herein, the term "sleep spindle" refers to is a burst of oscillatory brain activity visible on an EEG that predominantly occurs during stage 2 sleep. Sleep spindle activity spans a frequency range of about 12-16 Hz, e.g., about 12-14 Hz. The specific spectral features may be altered as a function of age, disease state, and other factors that contribute to inter-individual differences in brain activity patterns.

As used herein, the terms "enhance" and "increase" (and grammatical variants thereof) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

As used herein, the terms "inhibit" and "decrease" (and grammatical variants thereof) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the terms "oscillating current," "oscillating electric current" and "OEC" refer to an electric current that periodically reverses polarity.

As used herein, the term "psychiatric or neurological symptom associated with impairment of sleep spindle oscillation and/or impairment of cognitive function" refers to a disorder of the nervous system or a symptom of the disorder that is directly and/or indirectly caused by and/or leads to impairment of sleep spindle oscillation and/or impairment of cognitive function.

As used herein, the term "associated with premature birth" refers to a disorder or symptom that that is directly and/or indirectly caused by premature birth, e.g., 1, 2, 3, 4, 5, 6, 7, 8 or more weeks prior to full term, e.g., due to incomplete development of the brain or central nervous system.

As used herein, the term "associated with aging" refers to a disorder or symptom that that is directly and/or indirectly caused by the aging process.

As used herein, the term "subject" refers to both human subjects and animal subjects, including, but not limited to, mice, rats, rabbits, cats, dogs, pigs, horses, monkeys, apes, etc. The subject may be male or female. The subject may be of any suitable age, including infant, juvenile, adolescent, adult and geriatric ages. In some embodiments, the methods, devices and systems of the present invention may be used to induce physiological and/or psychological responses in a subject for medically diagnostic and/or therapeutic purposes. For example, the methods, devices and systems of the present invention may be used to diagnose and/or treat mammalian subjects, such as mice, rats, pigs and monkeys, for medical research or veterinary purposes.

As used herein, the terms "prevent," "preventing," and "prevention" (and grammatical variants thereof) refer to avoiding or delaying the onset of a disorder and/or a clinical symptom(s) in a subject relative to what would occur in the absence of the methods of the present invention. In some embodiments, prevention is complete, resulting in the total absence of the disorder and/or clinical symptom(s) (e.g., a total absence of growth of a pathogenic microbial strain). In some embodiments, prevention is partial, resulting in avoidance of some aspects of the disorder and/or clinical symptom(s) (e.g., prevention of positive symptoms (e.g., hallucinations) but not negative symptoms (e.g., flat affect)).

As used herein, the term "prevention effective amount" (and grammatical variants thereof) refers an amount that is sufficient to prevent and/or delay the onset of a disorder and/or clinical symptoms in a subject and/or to reduce and/or delay the severity of the onset of a disorder and/or clinical symptoms in a subject relative to what would occur in the absence of the methods of the invention. Those skilled in the art will appreciate that the level of prevention need not be complete, as long as some benefit is provided to the subject.

As used herein, the terms "therapeutically effective amount" and "therapeutically acceptable amount" (and grammatical variants thereof) refer to an amount that will elicit a therapeutically useful response in a subject. The therapeutically useful response may provide some alleviation, mitigation, or decrease in at least one clinical symptom in the subject. The terms also include an amount that will prevent and/or delay the onset of at least one clinical symptom in the subject and/or reduce and/or delay the severity of the onset of a clinical symptom in a subject relative to what would occur in the absence of the methods of the invention. Those skilled in the art will appreciate that the therapeutically useful response need not be complete or curative or prevent permanently, as long as some benefit is provided to the subject.

As used herein, the terms "treat," "treatment" and "treating" refer to reversing, alleviating, reducing the severity of and/or inhibiting the progress of a disease or disorder as described herein, or at least one symptom of a disease or disorder as described herein (e.g., treating tremors, bradykinesia, rigidity or postural instability associated with Parkinson's disease; treating hallucinations or delusions associate with schizophrenia; treating intrusive thoughts such as intrusive emotions, intrusive memories, nightmares and night terrors; treating hyperarousal symptoms such as exaggerated startle reactions, explosive outbursts, extreme vigilance, irritability, panic symptoms, sleep disturbances; treating tinnitus). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may be as an adjuvant treatment as further described herein.

As used herein, the term "treatment effective amount" (and grammatical variants thereof) refers to an amount that is sufficient to provide some improvement or benefit to the subject. Alternatively stated, a "treatment effective amount" is an amount that will provide some alleviation, mitigation, decrease, or stabilization in at least one clinical symptom in the subject. Those skilled in the art will appreciate that the therapeutic effects need not be complete or curative, as long as some benefit is provided to the subject.

As used herein, the term "procedural memory" refers to the part of long term memory that is responsible for knowing how to perform particular types of action, such as motor skills.

As used herein, the term "declarative memory" refers to the part of long term memory that can be consciously recalled such as facts and verbal knowledge.

As used herein, the terms "motor memory" and "muscle memory" refer to a form of procedural memory that involves consolidating a specific motor task into memory through repetition.

As used herein, the term "sleeping" refers to a long period of sleep, typically during the nocturnal sleep period.

As used herein, the term "napping" refers to a short period of sleep, typically taken during daylight hours as an adjunct to the usual nocturnal sleep period.

A first aspect of the invention relates to a method of improving memory or cognitive function in a subject, the method comprising: a) detecting a burst of oscillatory brain activity in the subject; and b) passing an oscillating current through the skull of the subject; thereby improving memory or cognitive function in the subject relative to memory or cognitive function in the absence of the method. In some embodiments, the improved memory is procedural memory and/or declarative memory. In some embodiments, the improved memory is motor memory. The improvement in memory or cognitive function may be any measurable improvement, e.g., an improvement of at least about 1%, 5%, 10%, 20%, 50%, 100%, or more relative to the level in the absence of the method of the invention. The level of memory or cognitive function may be measured by tests and techniques known in the art and as described herein. In some embodiments, the subject is a healthy subject in which an improvement in memory and/or cognitive function is desired. In some embodiments, the subject is one that has diminished memory and/or cognitive function (e.g., due to a disease or disorder) and in which an improvement in memory and/or cognitive function is desired or beneficial.

Another aspect of the invention relates to a method of modulating or enhancing the frequency of occurrence, structure, amplitude, and/or synchronization of sleep spindles in a subject, the method comprising: a) detecting a burst of oscillatory brain activity in the subject; and b) passing an oscillating current through the skull of the subject; thereby modulating or enhancing the frequency of occurrence, structure, amplitude, and/or synchronization of sleep spindles in the subject relative to the frequency of occurrence, structure, amplitude, and/or synchronization of sleep spindles in the absence of the method.

A further aspect of the invention relates to a method of treating a psychiatric or neurological symptom associated with impairment of sleep spindle oscillation and/or impairment of cognitive function in a subject in need thereof, the method comprising: a) detecting a burst of oscillatory brain activity in the subject; and b) passing an oscillating current through the skull of the subject; thereby treating the psychiatric or neurological symptom associated with sleep spindles in the subject. The psychiatric or neurological symptom may be any psychiatric or neurological symptom associated with impairment of sleep spindle oscillation and/or impairment of cognitive function. Examples include, without limitation, schizophrenia, dementia, Alzheimer's disease, autism, attention deficit hyperactivity disorder, sleep disturbance, or symptoms associated with premature birth (e.g., treatment to accelerate brain maturation) or aging.

For each of the methods of the invention, the burst of oscillatory brain activity may be detected in a brain region or regions and the oscillating current passed through the skull of the subject into the same brain region or regions. In other embodiments, the burst of oscillatory brain activity may be detected in a first brain region or regions and the oscillating current passed through the skull of the subject into a second brain region or regions different from the first brain region or regions.

In some such embodiments, the first and second brain regions (or groups of brain regions) are mutually exclusive (i.e., there is no overlap between the two regions (or groups of brain regions)). For example, cortical oscillations may be detected in the auditory cortex of the subject's brain and oscillating currents may be passed into the parietal cortex of the subject's brain (in a subject with schizophrenia, for example). In some such embodiments, the first and second brain regions (or groups of brain regions) partially overlap (i.e., some portion(s) of the subject's brain is part of both regions (or groups of brain regions)). For example, cortical oscillations may be detected in the auditory cortex and parietal cortex of the subject's brain and cortical oscillations may be passed into the parietal cortex of the subject's brain (in a subject with schizophrenia, for example).

The burst of oscillatory brain activity may be detected in any suitable region(s) of a subject's brain, including, but not limited to, the subject's occipital lobe, parietal lobe, temporal lobe, frontal lobe, visual cortex, auditory cortex, somatosensory cortex, premotor cortex, subject's motor cortex, prefrontal cortex, Wernicke's area, Broca's area, sensory association area, auditory association area and/or visual association area. In some embodiments, bursts of oscillatory brain activity are detected in two or more regions of the subject's brain concurrently. In some embodiments, bursts of oscillatory brain activity are detected in two or more regions of the subject's brain sequentially. For example, bursts of oscillatory brain activity may be concurrently/sequentially detected in the auditory cortex, the prefrontal cortex and/or temporoparietal cortex of the subject's brain (in a subject with schizophrenia, for example). In some embodiments, bursts of oscillatory brain activity are detected concurrently/sequentially in the subject's premotor cortex and/or primary motor cortex (in a subject with a movement disorder, for example). In some embodiments, the burst of oscillatory brain activity may be detected in the thalamus. Typically, sleep spindles are most prominent in fronto-central electrode leads, which covers frontal cortex, high-order association cortices, premotor and supplementary motor cortices. The temporal cortex may also serve as both a detection location and a stimulation target.

Oscillating currents may be passed through the skull of a subject into any suitable region(s) of the subject's brain, including, but not limited to, the subject's occipital lobe, parietal lobe, temporal lobe, frontal lobe, visual cortex, auditory cortex, somatosensory cortex, premotor cortex, motor cortex, prefrontal cortex, Wernicke's area, Broca's area, sensory association area, auditory association area and/or visual association area. In some embodiments, oscillating currents are passed through the skull of a subject into two or more regions of the subject's brain concurrently. In some embodiments, oscillating currents are passed through the skull of a subject into two or more regions of the subject's brain sequentially. For example, oscillating currents may be concurrently/sequentially passed through the skull of a subject into the auditory cortex, the prefrontal cortex and/or temporoparietal cortex of the subject's brain (to treat schizophrenia, for example). In some embodiments, oscillating currents are passed concurrently/sequentially through the skull of a subject into premotor cortex and/or primary motor cortex (to treat a movement disorder, for example).

In certain embodiments, the oscillating current may be passed through the skull of the subject in response to the burst of oscillatory brain activity, e.g., within a certain time after detection of the burst or overlapping in time with the burst. In some embodiments, the oscillating current may be passed through the skull of the subject in an interval between bursts of oscillatory brain activity. In some embodiments, the oscillating current may be passed through the skull of the subject at random time points with respect to the bursts of oscillatory brain activity.

In some embodiments, the burst of oscillatory brain activity may be detected and/or the oscillating current may be passed through the skull of the subject while the subject is sleeping. In other embodiments, the burst of oscillatory brain activity may be detected and/or the oscillating current may be passed through the skull of the subject while the subject is napping.

In one aspect of the methods of the invention, the burst of oscillatory brain activity is a sleep spindle. In some embodiments, the sleep spindle is a fast sleep spindle (e.g., about 14 Hz) and/or a slow sleep spindle (e.g., about 12 Hz). Sleep spindles may be detected by any technique known in the art and as described herein. In some embodiments, detecting a burst of oscillatory brain activity in the subject comprising identifying a sleep spindle in real-time. Identification may involve detection of sleep stage, e.g., by determination of the occurrence of rapid eye movement (REM) versus non-REM sleep, combined with online detection of sleep spindles in EEG recordings. The EEG recordings may be manipulated using thresholds and band-pass filtering to aid in the detection of sleep spindles.

In some embodiments, identifying the sleep spindle comprises: a) recording EEG signals of the subject; and b) filtering and processing the EEG signals to identify sleep spindles. The identification of sleep spindles may further comprise: a) determining the occurrence of REM versus non-REM sleep in the subject; and b) applying a threshold to a band-pass-filtered EEG recording. The detection of REM versus non-REM sleep is performed based on a clustering approach. A recording period may be assigned to non-REM sleep if: a) a 20 second moving-average wake index is below an awake index threshold; and b) a 20 second moving average REM index is below a REM index threshold. The wake index threshold and the REM index threshold are determined from a previous EEG recording of the subject, e.g., a recording from the previous sleep period such as the previous night (e.g., before treatment).

Calculations of the threshold values are based on logarithmic ratios of power in specific frequency bands of oscillatory brain activity. In some embodiments, the awake index is calculated using the formula $$\mathrm{Log(AlphaPower \times MuscleArtifact/FastDeltaPower)}$$

wherein: AlphaPower is the power from a band-pass-filtered signal with passband 8-12 Hz; MuscleArtifact is the power from a band-pass-filtered signal with passband 20-30 Hz; and FastDeltaPower is the power from a band-bass-filtered signal with passband 2-4 Hz; wherein power is determined from time windows, e.g., 10, 20, 30, 40, 50, or 60 second windows, e.g., 20 second windows.

In some embodiments, the REM index is calculated using the formula $$\mathrm{Log(BetaPower/DeltaPower)}$$

wherein: BetaPower is the power from a band-pass-filtered signal with passband 18-40 Hz; and DeltaPower is the power from a band-bass-filtered signal with passband 0.5-4 Hz; wherein power is determined from time windows, e.g., 10, 20, 30, 40, 50, or 60 second windows, e.g., 20 second windows.

In some embodiments, identifying the sleep spindle comprises: a) determining the presence of non-REM sleep; and b) determining a sigma power above a sigma threshold for a certain length of time, e.g., about 50 to about 500 msec, e.g., about 200 msec. In some embodiments, the sigma threshold is calculated using the formula $$\mathrm{mean\ sigma\ power \times sigma\ coefficient}$$

wherein: mean sigma power is the power from a band-pass-filtered signal with passband 11-16 Hz, which may be determined at the beginning of treatment; and sigma coefficient is determined from a previous recording of the subject and is chosen to maximize detection hits and minimize both false positives and false negatives. The parameters of these algorithms can be adjusted based on visual inspection of offline thresholding of the sigma power and subsequent visual inspection of the detected events to determine which correspond to true spindles. Alternatively, the statistical properties of the collection of detected events can be inspected to determine if the correct coefficient for thresholding has been used. Typical threshold values for the threshold are 3 to 4. Alternatively, offline methods, which cannot be used for real-time detection, can be used to validate the choice of sigma. For example, Ferrarelli et al., *Am. J. Psychiatry* 164:483 (2007) provided an algorithm which requires peak detection, which can be performed offline but not online. Comparison of the performance of such algorithms against the ones described here can be used for validation on sleep data collected for calibration of the real-time detection.

In some embodiments, identifying the sleep spindle comprises techniques other than or in addition to EEG recordings. Examples include, without limitation, recording electrocorticogram signals, auditory signals, visual signals, and/or somatosensory input signals.

Upon detection of a burst of oscillatory brain activity, an oscillatory current may be applied. In some embodiments, other types of non-invasive stimulation may be applied in addition to or instead of an oscillatory current, such as auditory, visual, or somatosensory input. In some embodiments, non-electrical stimulation may be advantageous, e.g., to cause less interference with real-time detection of brain activity and/or to limit side effects associated with applying electrical stimulation. For example, amplitude-modulated white noise may enhance and entrain sleep spindle activity for stimulation frequencies that mimic specific natural cortical oscillation frequencies, including delta, theta, alpha, sigma, beta, and gamma. Visual input may be, e.g., luminescence-modulated light. Somatosensory input may include gentle mechanical perturbation of the skin. In each of these types of non-invasive stimulation, the stimulation may be applied without disturbing the sleep of the subject.

The step of passing an oscillating current through the skull of the subject may be carried out using techniques known in the art and as described herein. In certain embodiments, passing an oscillating current through the skull of the subject comprises real-time application of transcranial alternating current stimulation (tACS). The tACS may be applied using any device and technique known in the art, such through the use of a voltage-controlled current source.

In certain embodiments, the oscillating current is passed through the skull of the subject using one or more pairs of electrodes placed (either directly or indirectly) in contact with the scalp of the subject. Electrodes may be placed at any suitable position(s) on the scalp, including, but not limited to, the positions defined by the International 10-20 System of Electrode Placement. In some embodiments, the electrodes are located at positions F3 and F4. In some embodiments, a return electrode is located at position Cz on the scalp.

The oscillating current that is applied may be in any pattern that is suitable for the methods of the invention. Any suitable characteristic of the oscillating current may be modulated in response to the burst of oscillatory brain activity in the subject's brain, including, but not limited to, the magnitude, frequency and/or duration of each OEC. In some embodiments, the oscillating current is frequency-matched and/or phase-matched to the burst of oscillatory brain activity.

In certain embodiments, the oscillating current is generated in response to specific parameters that are detected.

In some embodiments, one or more oscillating currents is passed through the skull of the subject responsive to the magnitude of the bursts of oscillatory brain activity, the difference between the magnitude of the bursts of oscillatory brain activity and a target value, whether the magnitude of the bursts of oscillatory brain activity has exceeded an upper threshold, the difference between the magnitude of the bursts of oscillatory brain activity and an upper threshold, whether the magnitude of the bursts of oscillatory brain activity has fallen below a lower threshold and/or the difference between the magnitude of the bursts of oscillatory brain activity and a lower threshold.

In some embodiments, one or more oscillating currents is passed through the skull of the subject responsive to the variance of the magnitude of the bursts of oscillatory brain activity over a defined period of time, the difference between the variance of the magnitude of the bursts of oscillatory brain activity and a target value, whether the variance of the magnitude of the bursts of oscillatory brain activity over a defined period of time has exceeded an upper threshold, the difference between the variance of the magnitude of the bursts of oscillatory brain activity over a defined period of time and an upper threshold, whether the variance of the magnitude of the bursts of oscillatory brain activity over a defined period of time has fallen below a lower threshold and/or the difference between the variance of the magnitude of the bursts of oscillatory brain activity over a defined period of time and a lower threshold.

In some embodiments, one or more oscillatory currents is passed through the skull of the subject responsive to the integral of the magnitude of the bursts of oscillatory brain activity, the difference between the integral of the magnitude of the bursts of oscillatory brain activity and a target value, whether the integral of the magnitude of the bursts of oscillatory brain activity over a defined period of time has exceeded an upper threshold, the difference between the integral of the magnitude of the bursts of oscillatory brain activity and an upper threshold, whether the integral of the magnitude of the bursts of oscillatory brain activity over a defined period of time has fallen below a lower threshold and/or the difference between the integral of the magnitude of the bursts of oscillatory brain activity and a lower threshold:

In some embodiments, one or more oscillatory currents is passed through the skull of the subject responsive to the temporal derivative of the magnitude of the bursts of oscillatory brain activity, the difference between the temporal derivative of the magnitude of the bursts of oscillatory brain activity and a target value, whether the temporal derivative of the magnitude of the bursts of oscillatory brain activity over a defined period of time has exceeded an upper threshold, the difference between the temporal derivative of the magnitude of the bursts of oscillatory brain activity and an upper threshold, whether the temporal derivative of the magnitude of the bursts of oscillatory brain activity over a defined period of time has fallen below a lower threshold and/or the difference between the temporal derivative of the magnitude of the bursts of oscillatory brain activity and a lower threshold.

In some embodiments, one or more oscillatory currents is passed through the skull of the subject responsive to the average magnitude of the bursts of oscillatory brain activity over a defined period of time, the difference between the average magnitude of the bursts of oscillatory brain activity over a defined period of time and a target value, whether the average magnitude of the bursts of oscillatory brain activity over a defined period of time has exceeded an upper threshold, the difference between the average magnitude of the bursts of oscillatory brain activity over a defined period of time and an upper threshold, whether the average magnitude of the bursts of oscillatory brain activity over a defined period of time has fallen below a lower threshold and/or the difference between the average magnitude of the bursts of oscillatory brain activity over a defined period of time and a lower threshold.

In some embodiments, one or more oscillatory currents is passed through the skull of the subject responsive to the variance of the average magnitude of the bursts of oscillatory brain activity over a defined period of time, the difference between the variance of the average magnitude of the bursts of oscillatory brain activity over a defined period of time and a target value, whether the variance of the average magnitude of the bursts of oscillatory brain activity over a defined period of time has exceeded an upper threshold, the difference between the variance of the average magnitude of the bursts of oscillatory brain activity over a defined period of time and an upper threshold, whether the variance of the average magnitude of the bursts of oscillatory brain activity over a defined period of time has fallen below a lower threshold and/or the difference between the variance of the average magnitude of the bursts of oscillatory brain activity over a defined period of time and a lower threshold.

In some embodiments, one or more oscillatory currents is passed through the skull of the subject responsive to the integral of the average magnitude of the bursts of oscillatory brain activity over a defined period of time, the difference between the integral of the average magnitude of the bursts of oscillatory brain activity over a defined period of time and a target value, whether the integral of the average magnitude of the bursts of oscillatory brain activity over a defined period of time has exceeded an upper threshold, the difference between the integral of the average magnitude of the bursts of oscillatory brain activity over a defined period of time and an upper threshold, whether the integral of the average magnitude of the bursts of oscillatory brain activity over a defined period of time has fallen below a lower threshold and/or the difference between the integral of the average magnitude of the bursts of oscillatory brain activity over a defined period of time and a lower threshold.

In some embodiments, one or more oscillatory currents is passed through the skull of the subject responsive to the temporal derivative of the average magnitude of the bursts of oscillatory brain activity over a defined period of time, the difference between the temporal derivative of the average magnitude of the bursts of oscillatory brain activity over a defined period of time and a target value, whether the temporal derivative of the average magnitude of the bursts of oscillatory brain activity over a defined period of time has exceeded an upper threshold, the difference between the temporal derivative of the average magnitude of the bursts of oscillatory brain activity over a defined period of time and an upper threshold, whether the temporal derivative of the average magnitude of the bursts of oscillatory brain activity over a defined period of time has fallen below a lower threshold and/or the difference between the temporal derivative of the average magnitude of the bursts of oscillatory brain activity over a defined period of time and a lower threshold.

In some embodiments, one or more oscillatory currents is passed through the skull of the subject responsive to whether the bursts of oscillatory brain activity within a first brain region are synchronized, to what degree the bursts of oscillatory brain activity in a first brain region are synchronized, the difference between the degree of synchronization of the bursts of oscillatory brain activity within a first brain region and a target value, whether the degree of synchronization of the bursts of oscillatory brain activity within a first brain region has exceeded an upper threshold, the difference between the degree of synchronization of the bursts of oscillatory brain activity within a first brain region and an upper threshold, whether the degree of synchronization of the bursts of oscillatory brain activity within a first brain region has fallen below a lower threshold and/or the difference between the degree of synchronization of the bursts of oscillatory brain activity within a first brain region and a lower threshold.

In some embodiments, one or more oscillatory currents is passed through the skull of the subject responsive to the variance of the degree of synchronization of the bursts of oscillatory brain activity within a first brain region over a defined period of time, the difference between the variance of the degree of synchronization of the bursts of oscillatory brain activity within a first brain region and a target value, whether the variance of the degree of synchronization of the bursts of oscillatory brain activity within a first brain region has exceeded an upper threshold, the difference between the variance of the degree of synchronization of the bursts of oscillatory brain activity within a first brain region and an upper threshold, whether the variance of the degree of synchronization of the bursts of oscillatory brain activity within a first brain region has fallen below a lower threshold and/or the difference between the variance of the degree of synchronization of the bursts of oscillatory brain activity within a first brain region and a lower threshold.

In some embodiments, one or more oscillatory currents is passed through the skull of the subject responsive to the average degree of synchronization of the bursts of oscillatory brain activity within a first brain region over a defined period of time, the difference between the average degree of synchronization of the bursts of oscillatory brain activity within a first brain region and a target value, whether the average degree of synchronization of the bursts of oscillatory brain activity within a first brain region has exceeded an upper threshold, the difference between the average degree of synchronization of the bursts of oscillatory brain activity within a first brain region and an upper threshold, whether the average degree of synchronization of the bursts of oscillatory brain activity within a first brain region has fallen below a lower threshold and/or the difference between the average degree of synchronization of the bursts of oscillatory brain activity within a first brain region and a lower threshold.

In some embodiments, one or more oscillatory currents is passed through the skull of the subject responsive to the variance of the average degree of synchronization of the bursts of oscillatory brain activity within a first brain region over a defined period of time, the difference between the variance of the average degree of synchronization of the bursts of oscillatory brain activity within a first brain region and a target value, whether the variance of the average degree of synchronization of the bursts of oscillatory brain activity within a first brain region has exceeded an upper threshold, the difference between the variance of the average degree of synchronization of the bursts of oscillatory brain activity within a first brain region and an upper threshold, whether the variance of the average degree of synchronization of the bursts of oscillatory brain activity within a first brain region has fallen below a lower threshold and/or the difference between the variance of the average degree of synchronization of the bursts of oscillatory brain activity within a first brain region and a lower threshold.

In some embodiments, one or more oscillatory currents is passed through the skull of the subject responsive to whether the bursts of oscillatory brain activity in a first brain region are synchronized with the bursts of oscillatory brain activity in a second brain region, to what degree the bursts of oscillatory brain activity in a first brain region are synchronized with the bursts of oscillatory brain activity in a second brain region, the difference between the degree of synchronization between the bursts of oscillatory brain activity in a first brain region and the bursts of oscillatory brain activity in a second brain region and a target value, whether the degree of synchronization between the bursts of oscillatory brain activity in a first brain region and the bursts of oscillatory brain activity in a second brain region has exceeded an upper threshold, the difference between the degree of synchronization between the bursts of oscillatory brain activity in a first brain region and the bursts of oscillatory brain activity in a second brain region and an upper threshold, whether the degree of synchronization of the bursts of oscillatory brain activity between the bursts of oscillatory brain activity in a first brain region and the bursts of oscillatory brain activity in a second brain region has fallen below a lower threshold and/or the difference between the degree of synchronization of the bursts of oscillatory brain activity between the bursts of oscillatory brain activity in a first brain region and the bursts of oscillatory brain activity in a second brain region and a lower threshold.

In some embodiments, one or more oscillatory currents is passed through the skull of the subject responsive to the variance of the degree of synchronization of the bursts of oscillatory brain activity between the bursts of oscillatory brain activity in a first brain region and the bursts of oscillatory brain activity in a second brain region over a defined period of time, the difference between the variance of the degree of synchronization of the bursts of oscillatory brain activity between the bursts of oscillatory brain activity in a first brain region and the bursts of oscillatory brain activity in a second brain region and a target value, whether the variance of the degree of synchronization of the bursts of oscillatory brain activity between the bursts of oscillatory brain activity in a first brain region and the bursts of oscillatory brain activity in a second brain region has exceeded an upper threshold, the difference between the variance of the degree of synchronization of the bursts of oscillatory brain activity between the bursts of oscillatory brain activity in a first brain region and the bursts of oscillatory brain activity in a second brain region and an upper threshold, whether the variance of the degree of synchronization of the bursts of oscillatory brain activity between the bursts of oscillatory brain activity in a first brain region and the bursts of oscillatory brain activity in a second brain region has fallen below a lower threshold and/or the difference between the variance of the degree of synchronization of the bursts of oscillatory brain activity between the bursts of oscillatory brain activity in a first brain region and the bursts of oscillatory brain activity in a second brain region and a lower threshold.

In some embodiments, one or more oscillatory currents is passed through the skull of the subject responsive to the average degree of synchronization of the bursts of oscillatory brain activity between the bursts of oscillatory brain activity in a first brain region and the bursts of oscillatory brain activity in a second brain region over a defined period of time, the difference between the average degree of synchronization of the bursts of oscillatory brain activity between the bursts of oscillatory brain activity in a first brain region and the bursts of oscillatory brain activity in a second brain region and a target value, whether the average degree of synchronization of the bursts of oscillatory brain activity between the bursts of oscillatory brain activity in a first brain region and the bursts of oscillatory brain activity in a second brain region has exceeded an upper threshold, the difference between the average degree of synchronization of the bursts of oscillatory brain activity between the bursts of oscillatory brain activity in a first brain region and the bursts of oscillatory brain activity in a second brain region and an upper threshold, whether the average degree of synchronization of the bursts of oscillatory brain activity between the bursts of oscillatory brain activity in a first brain region and the bursts of oscillatory brain activity in a second brain region has fallen below a lower threshold and/or the difference between the average degree of synchronization of the bursts of oscillatory brain activity between the bursts of oscillatory brain activity in a first brain region and the bursts of oscillatory brain activity in a second brain region and a lower threshold.

In some embodiments, one or more oscillatory currents is passed through the skull of the subject responsive to the variance of the average degree of synchronization of the bursts of oscillatory brain activity between the bursts of oscillatory brain activity in a first brain region and the bursts of oscillatory brain activity in a second brain region over a defined period of time, the difference between the variance of the average degree of synchronization of the bursts of oscillatory brain activity between the bursts of oscillatory brain activity in a first brain region and the bursts of oscillatory brain activity in a second brain region and a target value, whether the variance of the average degree of synchronization of the bursts of oscillatory brain activity between the bursts of oscillatory brain activity in a first brain region and the bursts of oscillatory brain activity in a second brain region has exceeded an upper threshold, the difference between the variance of the average degree of synchronization of the bursts of oscillatory brain activity between the bursts of oscillatory brain activity in a first brain region and the bursts of oscillatory brain activity in a second brain region and an upper threshold, whether the variance of the average degree of synchronization of the bursts of oscillatory brain activity between the bursts of oscillatory brain activity in a first brain region and the bursts of oscillatory brain activity in a second brain region has fallen below a lower threshold and/or the difference between the variance of the average degree of synchronization of the bursts of oscillatory brain activity between the bursts of oscillatory brain activity in a first brain region and the bursts of oscillatory brain activity in a second brain region and a lower threshold.

In some embodiments, one or more oscillatory currents is passed through the skull of the subject responsive to a signal generated in response to analysis of bursts of oscillatory brain activity.

Oscillatory currents may be generated in real-time. In some embodiments, one or more oscillatory currents is generated in real-time responsive to analysis of bursts of oscillatory brain activity.

Methods of the present invention may further comprise administering at least one pharmaceutical agent to the subject. In some embodiments, the at least one pharmaceutical agent is administered prior to passage of the oscillatory current through the skull of the subject. In some embodiments, the at least one pharmaceutical agent is administered concurrently with passage of the oscillatory current through the skull of the subject. In some embodiments, the at least one pharmaceutical agent is administered following passage of the oscillatory current through the skull of the subject. In some embodiments, the at least one pharmaceutical agent comprises a plurality of pharmaceutical agents.

Any suitable pharmaceutical agent may be administered to the subject, including, but not limited to, antidepressants (e.g., selective serotonin reuptake inhibitors (e.g., fluoxetine, paroxetine, citalopram, escitalopram, sertraline), monoamine oxidase inhibitors (e.g., isocarboxazid, phenelzine)), stimulants (e.g., caffeine, methylphenidate, dexmethylphenidate, dextroamphetamine, levoamphetamine, methamphetamine, modafinil), antipsychotics (e.g., risperidone, quetiapine, olanzapine, lurasidone, aripiprazole, asenapine, butyrophenones (e.g., benperidol, droperidol, haloperidol), paliperidone, ziprasidone, clozapine, amisulpride, amoxapine, blonanserin, iloperidone, melperone, perospirone, sertindole, zotepine, perphenazine, phenothiazines (e.g., chlorpromazine, cyamemazine, fluphenazine, levomepromazine, mesoridazine, pericyazine, perphenazine, prochlorperazine, promazine, promethazine, thioridazine, trifluoperazine, triflupromazine), thioxanthenes (e.g., chlorprothixene, clopenthixol, flupenthixol, thiothixene, zuclopenthixol), loxapine, pimozide, sulpiride, trimipramine), mood stabilizers (e.g., lithium, valproate, carbamazepine, oxcarbazepine, lamotrigine, gabapentin, pregabalin, topiramate, olanzapine), anxiolytics, anti-ADD and ADHD agents (e.g., amphetamine, dextroamphetamine, lisdexamfetamine, methylphenidate, clonidine, atomoxetine, guanfacine), anti-dementia agents (e.g., donepezil, galantamine, rivastigmine, memantine), hallucinogens (e.g., LSD, psilocybin, mescaline, ibogaine, cannabis, dimethyltryptamine), hypnotics (e.g., diazepam, nitrazepam, zolpidem, zopiclone, zaleplon, chlordiazepoxide, alprazolam, temazepam, clonazepam, lorazepam), sedatives (e.g., barbiturates (e.g., amobarbital, pentobarbital, secobarbital, phenobabrital), antihistamines (diphenhydramine, dimenhydrinate, doxyamine, mirtazapine, promethazine), herbal sedatives (e.g., cannabis, kava, valerian, validol), chloral hydrate, trazodone, alcohol, opiates, glutethimide), and anesthetics (e.g., desflurane, enflurane, halothane, isoflurane, methoxyflurane, nitrous oxide, sevoflurane, xenon, amobarbital, methohexital, thiamylal, thiopental, etomidate, ketamine, propofol, alfentanil, fentanyl, remifentanil, sufentanil, buprenorphine, butorphanol, hydromorphone, diacetyl morphine, levorphanol, meperidine, methadone, morphine, nalbuphine, oxycodone, oxymorphone, pentazocine, muscle relaxants (e.g., succinylcholine, decamethonium, mivacurium, rapacuronium, atracurium, cisatracium, rocuronium, vecuronium, alcuronium, doxacurium, gallamine, metocurine, pancuronium, pipecuronium, tubocurarine)).

Pharmaceutical agents may be administered to the subject in any suitable amount(s). In some embodiments, each pharmaceutical agent is administered to the subject in a therapeutically effective amount. In some embodiments, each pharmaceutical agent is administered to the subject in an amount that would not be therapeutically effective if not combined with passage of the oscillatory current through the skull of the subject.

Given the teaching provided by the present disclosure and the general knowledge available to those skilled in the art with respect to pharmaceutical agents, those skilled in the art will understand how to select and/or optimize administration of the pharmaceutical agent(s) to achieve a therapeutic effect and/or to enhance the therapeutic effect of the oscillatory current.

Methods of the present invention may further comprise administering one or more psychotherapies to the subject. In some embodiments, the at least one psychotherapy is administered prior to passage of the oscillatory current through the skull of the subject. In some embodiments, at least one psychotherapy is administered concurrently with passage of the oscillatory current through the skull of the subject. In some embodiments, the at least one psychotherapy is administered following passage of the oscillatory current through the skull of the subject.

Any suitable psychotherapy may be administered to the subject, including, but not limited to, art therapy, behavioral modification, behavioral therapies, cognitive analytic therapy, cognitive behavior therapy, coherence therapy, dialectical behavior therapy, existential therapy, family therapy, holistic psychotherapy, hypnotherapy, marriage counseling, multimodal therapy, music therapy, pastoral counseling, play therapy, primal therapy, process-oriented psychology, prolonged exposure therapy, psychoanalysis, relationship counseling, reprogramming, sexual identity therapy, social therapy, systematic desensitization, systemic therapy, transference focused psychology, twelve step programs and wilderness therapy. Psychotherapies may be administered to the subject according to any suitable protocol.

Given the teaching provided by the present disclosure and the general knowledge available to those skilled in the art with respect to psychotherapy, those skilled in the art will understand how to select and/or optimize the administration of the psychotherapy(ies) to achieve a therapeutic effect and/or to enhance the therapeutic effect of the oscillatory current.

Methods of the present invention may modulate cortical activity in any suitable manner, including, but not limited to, inhibiting bursts of oscillatory brain activity, enhancing bursts of oscillatory brain activity, increasing the coherence of bursts of oscillatory brain activity (e.g., increasing the coherence of bursts of oscillatory brain activity within a brain region and/or increasing the coherence of bursts of oscillatory brain activity in a first brain region with bursts of oscillatory brain activity in one or more different brain regions) and decreasing the coherence of bursts of oscillatory brain activity (e.g., decreasing the coherence of bursts of oscillatory brain activity within a brain region and/or decreasing the coherence of bursts of oscillatory brain activity in a first brain region with bursts of oscillatory brain activity in one or more different brain regions).

Given the teaching provided by the present disclosure and the general knowledge available to those skilled in the art with respect to cortical states and bursts of oscillatory brain activity, those skilled in the art will understand how to select and/or optimize oscillatory currents to achieve the desired effect(s).

Methods of the present invention may be used to prevent and/or treat any suitable psychiatric or neurological disorder, including, but not limited to, aphasias (e.g., receptive aphasias, expressive aphasias, pure alexia), apraxias (e.g., ideomotor apraxia, conceptual apraxia, gait apraxia), agnosias (e.g., akinetopsia, anosognosia, visual agnosia, auditory agnosia, verbal agnosia, astersognosis, phoagnosia, prosopagnosia, alexia, tactile agnosia, time agnosia) and amnesias (e.g., dissociative amnesia, epileptic amnesia). In some embodiments, methods of the present invention are used to treat an anxiety disorder such as social anxiety disorder, obsessive-compulsive disorder, post-traumatic stress disorder, generalized anxiety disorder, situational anxiety, separation anxiety or a phobia (e.g., agoraphobia). In some embodiments, methods of the present invention are used to treat an eating disorder such as anorexia nervosa or bulimia nervosa. In some embodiments, methods of the present invention are used to treat a mood disorder such as a bipolar disorder or a depressive disorder. In some embodiments, methods of the present invention are used to treat a personality disorder such as schizoid, paranoid, schizotypal, antisocial, borderline, histrionic, narcissistic, avoidant, dependent or obsessive-compulsive personality disorder. In some embodiments, methods of the present invention are used to treat a psychotic disorder such as schizophrenia. In some embodiments, methods of the present invention are used to treat a substance use disorder such as substance dependence and substance abuse. In some embodiments, methods of the present invention are used to treat a somatoform disorder such as body dysmorphic disorder, hypochondriasis, pain disorder or conversion disorder. In some embodiments, methods of the present invention are used to treat a developmental disorder such as an autism spectrum disorder (e.g., Asperger syndrome) or attention deficit disorder. In some embodiments, methods of the present invention are used to treat a neurodegenerative disease such as Alzheimer's disease, Parkinson's disease or Huntington's disease. In some embodiments, methods of the present invention are used to treat a seizure disorder such as epilepsy. In some embodiments, methods of the present invention are used to treat a movement disorder such as bradykinesia, chorea (e.g., Huntington's disease), Parkinson's disease, tic disorders (e.g., Tourette's Syndrome), multiple sclerosis, amyotrophic lateral sclerosis, tremors or cerebral palsy. In some embodiments, methods of the present invention are used to treat a sleep disorder such as hypersomnias (e.g., narcolepsy), parasomnias (e.g., sleep terrors, sleep enuresis, somniloquy) or insomnia. In some embodiments, methods of the present invention are used to treat dementia.

Methods of the present invention may be used to prevent and/or treat psychiatric or neurological disorders in any suitable manner, including, but not limited to, inhibiting and/or delaying onset of a disorder/symptom, inhibiting and/or delaying reoccurrence of a disorder/symptom, decreasing the length of time from onset of a disorder/symptom to remission of the disorder/symptom, increasing the amount of time spent in remission, increasing the number of symptom-free days, decreasing the severity of one or more symptoms. In some embodiments, inhibition of the disorder/symptom is complete, resulting in the total absence of the disorder and/or clinical symptom(s) (e.g., a total absence of hallucinations). In some embodiments, inhibition is partial, resulting in reduced severity and/or delayed onset of the disorder and/or clinical symptom(s) (e.g., a reduction in the frequency of hallucinations).

Methods of the present invention may be used to decrease the length of time from onset of a disease/symptom to remission of the disease/symptom by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more as compared to a control subject/population (e.g., a subject/population to which the oscillatory current was not administered).

Methods of the present invention may be used to decrease the severity of one or more symptoms of a psychiatric or neurological disorder by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more as compared to a control subject/population (e.g., a subject/population to which the oscillatory current was not administered).

Methods of the present invention may be used to increase the amount of time spent in remission from a psychiatric or neurological disorder by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more as compared to a control subject/population (e.g., a subject/population to which the oscillatory current was not administered).

Methods of the present invention may be used to increase the number of symptom-free days by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more as compared to a control subject/population (e.g., a subject/population to which the oscillatory current was not administered).

Methods of the present invention may be used in the chronic treatment of psychiatric or neurological disorders.

Given the teaching provided by the present disclosure and the general knowledge available to those skilled in the art with respect to psychiatric and neurological disorders, those skilled in the art will understand how to select and/or optimize methods of the present invention to prevent and/or treat a given disease/symptom.

Methods of the present invention may be used to enhance any suitable cognitive trait, including, but not limited to, alertness, awareness, memory accuracy, memory longevity, information processing accuracy and information processing speed. In some embodiments, methods of the present invention are used to enhance problem-solving ability.

Methods of the present invention may be used to enhance one or more cognitive traits by at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more.

The methods of the present invention can be carried out using any cortical stimulation device capable of detecting bursts of oscillatory brain activity and/or coherence (e.g., coherence between bursts of oscillatory brain activity of a specific frequency (or group of frequencies)) in a subject and/or passing one or more oscillatory currents through the skull of a subject. In some embodiments, the device provides transcranial alternating current stimulation (tACS) and or transcranial direct current stimulation (tDCS). Suitable devices are known in the art, e.g., as described in WO 2015/069632 (incorporated by reference herein in its entirety).

Having described the present invention, the same will be explained in greater detail in the following examples, which are included herein for illustration purposes only, and which are not intended to be limiting to the invention.

Example 1

Experimental Procedures
  Participants:

17 healthy male volunteers (18-35 years, 22±4 years, Mean±SD) were recruited by advertisement at the University of North Carolina at Chapel Hill and participated in the main experiment. This study was approved by the UNC IRB and all participants signed written consent prior to participation. Only male participants were included to reduce variability in sleep spindle measures and memory induced by the menstrual cycle in females (Fogel et al., *Hum. Brain Mapp.* 35:3625 (2014); Driver et al., *J. Clin. Endocrinol. Metab.* 81:728 (1996)). None of the participants had chronic diseases, were using psychoactive agents or other medications, or reported family history of psychopathology as verified with a telephone and questionnaire screening. Furthermore, participants were non-smokers and right-handed. It was verified during a screening night that participants were good, healthy sleepers (sleep efficiency (percentage N1, N2, N3 and REM of total time in bed [lights off to lights on]≥80%). Participants were required to maintain a regular sleep-wake schedule (~8 h time in bed, according to scheduled bedtime in the lab) and abstain from caffeine, naps, and alcohol at least 2 days before the study nights to ensures stable conditions. Compliance with the instructions was confirmed by visual inspection of wrist-worn actometer data (Geneactiv recorder, Activinsights Ltd., Kimbolton, UK) and/or sleep logs. One participant did not comply with these rules (>2 h deviation from scheduled bedtime) and reported food poisoning and medication use before the second study night. This participant was excluded completely from our analysis, resulting in a final sample size of 16 participants.

Procedure:

After a screening night each participant underwent two experimental conditions, one with all-night feedback-controlled transcranial alternating current stimulation (FB-tACS) spindle stimulation (verum) and one sham condition, in a randomized, balanced cross-over design. Both experimental sessions were at least 5 days apart. For both conditions, participants were trained in the evening on a declarative word-pair association task and a motor sequence tapping task (learning block started ~1.5 h before individually preferred bedtime). As done in previous studies the order of the memory tasks was kept constant (declarative learning task, procedural learning task) to increase standardization and to minimize variability (Feld et al., *Sleep* 36:1317 (2013)). Even though this approach might have led to order effects since consolidation of declarative and procedural tasks can influence each other if performed directly after each other, the possible interference between both tasks does not eliminate the beneficial effect memory (Brown et al., *J. Neurosci.* 27:10468 (2007)). To further minimize this possible interference effect longer breaks were used between the tasks (~10 minutes) as was done previously (Feld et al., *Sleep* 36:1317 (2013)). After the initial training of the memory tasks, participants had 8 h of polysomnographically recorded sleep (EEG, EOG and EMG). They were retested in the morning on the memory tasks (~50 min after wake up time) to assess sleep-dependent declarative and motor memory consolidation. To exclude a general effect of time of day or stimulation condition on sustained attention or vigilance, participants had to perform the psychomotor vigilance task (PVT) for 5 minutes (Khitrov et al., *Behavior Res. Meth.* 46:140 (2014)) and rate their sleepiness, motivation, and how focused they were on a visual analogue scale right before memory assessment. Furthermore, participants had to complete a subjective sleep quality questionnaire in the morning (results are provided in Table 3). Participants and research assistants administering the behavioral tasks (memory tasks, PVT) were blinded to the stimulation condition.

Memory Task:

Sleep-dependent changes in declarative memory were assessed using the paired associate learning (word-pair) task (Marshall et al., Nature 444:610 (2006); Ngo et al., Neuron 78:545 (2013)). Two parallel word-pair lists provided by Marshall et al., Nature 444:610 (2006) were used for the two nights (in a randomized order). Fifty moderately semantically related word-pairs were presented on a computer screen for 4 s each, separated by an inter-stimulus interval of 100 ms. Two dummy pairs of words (no recall required) at the beginning and end of each list were used to buffer primacy and recency effects (Plihal et al., J. Cognitive Neurosci. 9:534 (1997)). Following presentation, participants performed an immediate cued-recall, where the first word of each word-pair was presented in random order and the second one had to be recalled. After participants entered their answer, feedback for accuracy was provided and the correct word-pair was presented again for two seconds. This recall procedure was repeated in the morning (delayed recall). Overnight retention was defined as the difference in correct answers between delayed and immediate recall.

To assess sleep-dependent motor memory consolidation a motor sequence tapping task adapted from Walker et al., Neuron 35:205 (2002) was utilized. Two parallel versions were used in a balanced and randomized order for the two experimental conditions. In this task, participants were required to repeatedly complete a five-element sequence (e.g., 4-1-3-2-4) with their left hand (non-dominant) as fast and accurately as possible. Participants responded on a high-precision keyboard (millisecond polling) to ensure accurate response time measurement between individual key-presses. The training in the evening consisted of twelve 30-s blocks and the retest in the morning of three 30-s blocks. All blocks were interspersed with 30-s breaks. The sequence was continuously displayed on a screen in front of participants to prevent a working memory component. Performance improvements in motor tasks are reflected as an increase of speed and accuracy. Speed was assessed by calculating the mean tapping time (response time between correct key presses (Brawn et al., J. Neurosci. 30:13977 (2010); Fogel et al., Hum. Brain Mapp. 35:3625 (2014)). Outlying response times were excluded by removing values deviating more than 3 times the SD from the mean. The number of correct sequences tapped (combination between speed and accuracy measure) and number of errors (measure for accuracy) was further assessed. Post-training performance was defined as the mean of the last 2 trials in the training session and retrieval performance was defined as the mean of the first 2 trials during retest according to literature (Walker et al., Neuron 35:205 (2002); Lustenberger et al., Brain Stimul. 6:805 (2013)). Sleep-dependent performance change in this motor task was calculated as the absolute difference between the morning retrieval performance and the evening post-training performance ([retrieval performance−post-training performance]).

Spindle FB-tACS:

To perform real-time sleep spindle detection and stimulation the previously-described custom EEG-tACS feedback control system (Boyle et al., In Neural Engineering (NER), 2013 6th International IEEE/EMBS Conference on. (IEEE), pp. 140-143 (2013)) that integrates commercially available hardware and open-source software was modified (FIG. 2A). Online spindle detection and stimulation (FIGS. 2A and 2B) was performed using Real-Time eXperiment Interface (RTXI) software (Lin et al., In Engineering in Medicine and Biology Society (EMBC), 2010 Annual International Conference of the IEEE. (IEEE), pp. 4160 (2010)) and two NeuroConn DC-STIMULATOR PLUS devices (NeuroConn Ltd., Ilmenau, Germany). Two 3×3 cm stimulation electrodes were placed bi-frontally (one at the F3 10-20 site and one at the F4 10-20 site, each connected to one of the two stimulators) and a shared 5×5 cm stimulation electrode was placed at Cz (connected to both of the stimulators) using conductive paste (FIG. 1B).

The raw Fz-CPz signal (sampled at 500 Hz, recorded with BIOPAC Systems, Inc., Goleta, Calif.) was used as the input signal to the control system. Fz-CPz signal was first filtered into various component frequency bands (e.g., delta band, alpha band). Fz-CPz was chosen because sleep spindles are predominant over frontal and centro-parietal regions and therefore the number of spindle detections can be optimized. This was further the reason for positioning the stimulation electrodes on frontal and central regions. Prevailing sigma band activity was used as the primary indicator of sleep spindle activity. Since sigma activity and awake alpha fluctuations overlap in the frequency domain, custom sleep depth metrics were calculated from the Fz-CPz signal to determine periods of NREM sleep to minimize "sleep spindle" detections during REM or wakefulness. For each frequency band except the sigma band, a 20-s moving average was applied to the square of the signal as a measure of temporally bound average power. These numbers were used at each sample point to calculate the instantaneous REM index and wakefulness index. The REM index was calculated as a ratio between beta and delta power, the wake index as a product of alpha and beta power in ratio to delta power. Each index is based on spectral power components prevailing during those vigilance states (Berthomier et al., Sleep 30:1587 (2007); Jobert et al., Sleep 17:37 (1994); Kuwahara et al., Electroencephalogr. Clin. Neurophysiol. 70:220 (1988); Virkkala et al., Neurosci. Meth. 166:109 (2007)). These two values were then compared with thresholds determined during the screening night. Screening night EEG was scored in 20-s epochs by an expert sleep scorer, and REM and wake indices were calculated for these static 20-s windows (average power calculated for the aforementioned frequency bands) using the same formulas as online detection. Thresholds were then visually determined by the scorer based on scatter plots to allow maximal NREM epoch detection while maintaining an extremely low false positive rate (FIG. 2C). The screening night EEG was further used to determine the sigma activity threshold for each participant. First, the sigma-bandpassed Fz-CPz signal was rectified and peaks were detected. A moving window of 5 peaks of rectified sigma band activity (~200 ms) was then used as the measure of spindle amplitude. Spindle-like electrical stimulation was triggered (1 mA 12 Hz sine wave, 1-s duration at maximum amplitude, 0.25-s linear ramp up and 0.25-s linear ramp down) whenever each of the 5 peaks in the rectified sigma band window exceeded the individualized sigma activity threshold, as long as the instantaneous REM and wake index values were below their respective thresholds. Each electrical stimulation was followed by a 6.5 second timeout, where no filter outputs were included in sigma amplitude thresholding or REM and wakefulness index calculation. During verum night, sigma activity thresholds were set to a multiple of the average sigma amplitude during a 10 minute baseline recording (first continuous 10 minutes of NREM sleep based on experts online scoring) of the study night sleep EEG (thresholds screening: 8.87±0.79 µV; verum: 8.33±0.65 µV; thresholds were highly correlated:

r(14)=0.94, p<0.001). The value of this multiplier was determined from the screening night EEG as the multiplier that maximized concordance between our online algorithm and a commonly used offline spindle detection algorithm from the literature (Ferrarelli et al., *Am. J. Psychiatry* 164:483 (2007)) (algorithm parameters were 5× mean sigma amplitude for upper threshold, 2× mean sigma amplitude for lower threshold; a detailed description can be found in Lustenberger et al., *Sleep* 38:1093 (2015) and Ferrarelli et al., *Am. J. Psychiatry* 164:483 (2007). The multiplier that resulted in the maximal F-score was selected (Warby et al., *Nat. Methods* 11:385 (2014)), which reflects the harmonic mean of precision and recall between the offline algorithm spindle detection and our novel online spindle detection. Specifically, two types of precision and recall metrics were obtained. Type 1 was according to Warby et al., *Nat. Methods* 11:385 (2014), and Type 2 extended Type 1 to include stronger weighting for wake and REM spindles in the precision score and excluded the timeout rule for the recall metric. Those different types of precision and recall metrics resulted in two different types of F-scores that were combined to a final F-score used to determine the mean multiplier (see FIG. 2D for an example and Table 1 for results). The sigma activity threshold was defined as the average sigma amplitude times the previously determined individual multiplier. To avoid possible spindle stimulations (verum condition) during epochs of low sleep pressure and an acute effect of stimulation on memory performance, the system was switched into sham mode for the 30 minutes prior to rise time in the morning. During sham experimental nights, no electrical stimulation was delivered to the participants. However, they had the exact same electrode setup to ensure blinding to the condition.

TABLE 1

F-scores, precision and recall of spindle detection during screening night (n = 16)

| | Mean (SEM) |
|---|---|
| F-score Final | 0.60 (0.01) |
| Fscore Type 1 | 0.54 (0.01) |
| Fscore Type 2 | 0.65 (0.02) |
| Precision Type 1 | 0.84 (0.02) |
| Precision Type 2 | 0.69 (0.02) |
| Recall Type 1 | 0.40 (0.01) |
| Recall Type 2 | 0.62 (0.02) |

Sleep EEG Recording and Processing:

All night whole-head EEG (21 channels), submental EMG, and EOG were recorded with a GRASS amplifier and sampled at 400 Hz. EEG electrodes were applied at 10-20 positions (except F3, F4 were placed 2 cm posterior due to stimulation electrodes). Recording reference electrode was placed at Oz. Sleep staging was performed based on 20-s epochs according to standard criteria (Iber et al., The AASM Manual for the scoring of sleep and associated events, (Westchester, Ill., USA: American Academy of Sleep Medicine (2007))). All channels were offline re-referenced to linked mastoids.

To evaluate the effect of FB spindle-tACS on the EEG, spectrograms were calculated after the spindle detection between sham (only detection, no stimulation) and verum triggers (1.5 s of spindle tACS). Specifically, triggers obtained during the verum night were based on the actual stimulation artifacts and for the sham night a mock online detection of spindles (according to verum night) was performed offline using the spindle threshold obtained during the verum night. The tACS produced pronounced artifacts in the EEG for the first ~2 s of the EEG and around 5 s after stimulation (caused by internal source switching in the stimulator). The data was therefore cut and linearly interpolated for the first 2 s after stimulation and between 4.3 and 6 s after stimulation for both verum and sham conditions. This blanking is helpful as the wavelet analysis would otherwise smear the pronounced artifact over the entire (artifact free) interval. Spectrograms were then calculated from 2 s before to 7 s after the spindle triggers at 0.25 Hz resolution between 0.5 Hz and 20 Hz by convolving with Morlet wavelets of corresponding frequencies. Further analysis to compare the spectrograms between sham and verum triggers was restricted to the longest artifact free window after stimulation (2 s to 4.3 s after stimulation). One participant had to be excluded for this analysis due to poor Fz-CPz signal quality during the sham night, preventing accurate spindle detection/trigger definition. Only triggers during NREM sleep and without any visually identified artifacts between 2 and 4.3 s were included in the analysis (see Table 2 for details). The triggers were further into N2 and N3 for two reasons: (1) because significantly more triggers in N3 were obtained during sham night than verum night (n=15, sham: 254±35, verum: 191±37, p=0.02, see Table 2) and (2) to compare the effect of stimulation between light (N2) and deep sleep (N3), and different levels of thalamo-cortical hyperpolarization (N3 has more pronounced hyperpolarization than N2)(Andrillon et al., *J. Neurosci.* 31:17821 (2011); Nunez et al., *Neuroscience* 48:75 (1992)). Channels with bad signal quality were excluded (on average 1.2 of 15 participants excluded per channel, range 0-3).

For the sham night EEG, the Hilbert amplitude was calculated in the spindle frequency range (Chebyshev filter with pass-band lower cutoff of 10 Hz and higher cutoff at 16 Hz) for non-interpolated data of Fz-CPz (online detection channel) to ensure that spindle activity was prevailing and significantly increased around the trigger onset. All artifact-free triggers were included during NREM sleep and all 16 participants (within-subject statistics) for this analysis. The Hilbert transform has the capability to specify the instantaneous amplitude in a specific frequency range (when signal is first band-pass filtered) with millisecond time resolution (Hahn, S. L. (1996). Hilbert transforms in signal processing, (Boston: Artech House on Demand)).

For spindle characterization during the sham night the EEG was first filtered between 0.5 and 40 Hz and down sampled it to 128 Hz. Artifacts were then semi-automatically identified based on power values in the delta and beta range (for details see Lustenberger et al., *Sleep* 38:1093 (2015)). Thereafter an automatic offline spindle detection was applied using a similar approach as described above (Online spindle/NREM detection). A detailed description of the applied procedure can further be found in Ferrarelli et al., *Am. J. Psychiatry* 164:483 (2007); Lustenberger et al., *Sleep* 38:1093 (2015). The signal was band-pass filtered between 10 and 16 Hz to allow a spindle characterization in a broad frequency range (11-16 Hz) and used an upper threshold of 5× the mean and a lower threshold of 2× the mean as described above. The applied algorithm provides different spindle measures and sleep spindle density (number/min), duration and maximal spindle amplitude for different frequency bins were focused on during NREM sleep (see Lustenberger et al., *Sleep* 38:1093 (2015) for details).

Statistics:

Data are expressed as mean±s.e.m if not otherwise stated. p-values<0.05 were considered significant and 0.1>p≥0.05 were considered trend level.

To estimate the effect of FB tACS on memory, sleep stages, vigilance, and responses to questionnaires, a robust linear mixed model analysis (Koller, M. (2014). robustlmm: Robust Estimating Equations and Examples; Koller, M. (2014). Package 'robustlmm') was applied. An advantage of using robust statistical methods is that they provide accurate p-values even if some assumptions (e.g., normal distribution) are violated (Erceg-Hurn et al., *American Psychologist* 63:591 (2008)). The Kenward-Roger approximation was used to estimate F and p-values (Halekoh et al., *J. Statistical Software* 59:1 (2014)) [S18]. To assess the influence of FB-tACS on memory consolidation (overnight difference), condition (verum vs. sham), session (night 1 vs. night 2) and task form (version A vs. version B) were included as fixed factors and participant as a random factor (repeated measure) into the model. If condition had a significant influence on memory consolidation an additional robust linear mixed model (same fixed and random factors) was performed to analyze the effect of stimulation on evening performance to exclude the possibility that the effect on memory consolidation is driven by baseline differences.

The effects of stimulation on sleep stages, vigilance (PVT mean reaction time), and questionnaires were assessed by including condition and session as fixed factors and participant as random factors in the robust linear mixed model (see Table 3 for results).

Spectrograms were compared between the sham and verum condition using a two-sided paired t-test for each timepoint (2 ms resolution) and frequency bin (0.25 Hz resolution) using MATLAB. To show that spindle Hilbert amplitude was significantly increased around the spindle detection trigger, within individual subject comparisons were performed of all trials for each timepoint to the mean spindle Hilbert amplitude of the overall epoch (−2.5 s before to 7.5 s after the trigger, only during sham condition) for each trial using unpaired t-tests (one-sided, right tailed) in MATLAB.

Correlation analyses were performed using Pearson's correlations. To investigate the relationship between different spindle characteristics (density and duration) and overnight performance gains, a hierarchical cluster analysis was further conducted on the r-values of the two dimensional correlation matrices (channels/electrodes×frequency bins). To do so, a 2D hierarchical clustering of the Euclidean distances between all 11 frequency bins (11 to 16 Hz with 0.5 Hz bins) and all 18 EEG derivations was performed based on their correlation (r-values) with the overnight gain in motor sequence speed using the "clustergram" function provided by MATLAB (see Lustenberger et al., *Sleep* 38:1093 (2015) for details). This approach was used to demonstrate in an objective way the frequency bins that showed similar correlations between spindle characteristics and motor memory consolidation for multiple EEG channels and were clearly separated from other frequencies. A cut-off of 1.3 was used for the Euclidean distance because the derived frequency clusters were the most meaningful ones across all dendrograms. To control for multiple comparisons in the topographical analyses (FIGS. 6 and 9) statistical nonparametric mapping (SnPM) was applied using suprathreshold cluster analyses (Ferrarelli et al., *Am. J. Psychiatry.* 167:1339 (2010); Nichols et al., *Hum. Brain Mapp.* 15:1 (2002); Lustenberger et al., *Schizophr. Bull.* 41:522 (2015)). Thus, clusters of neighboring electrodes above/below the highest/lowest trend-level r-value or t-value (p<0.1) that were at or above the $95^{th}$ percentile cluster size given by the permutation analysis were considered significant, above or at $90^{th}$ percentile as trend-level.

Results 16 male participants underwent a screening night and thereafter completed two study nights (randomized, counterbalanced crossover design), one with spindle FB-tACS (verum) and one without stimulation (sham). During both study nights participants performed an associative word-pair (declarative) and motor sequence tapping task (procedural) in the evening and were retested in the morning to assess sleep-dependent memory consolidation. All-night polysomnographic recordings (8 h, EEG, EOG, and EMG) were collected. Participant-adapted thresholds based on spectral power values and spindle characteristics obtained during the screening night EEG (Fz-Cpz) were used to simultaneously evaluate in real-time if (1) the participant was in NREM sleep and (2) spindle activity reached an individually defined threshold (FIG. 1A and FIGS. 2A-2E) during the study nights. If (1) and (2) were met, short epochs of alternating currents with a spindle-like waveform were applied bi-frontally during the verum condition (FIG. 1B). Participants were successfully blinded to stimulation condition, as the 2 participants that reported sensation of electrical stimulation did so during the sham night. One subject was excluded from stimulation-related EEG analysis due to bad signal quality.

Figures 3A, 3B, 3C:
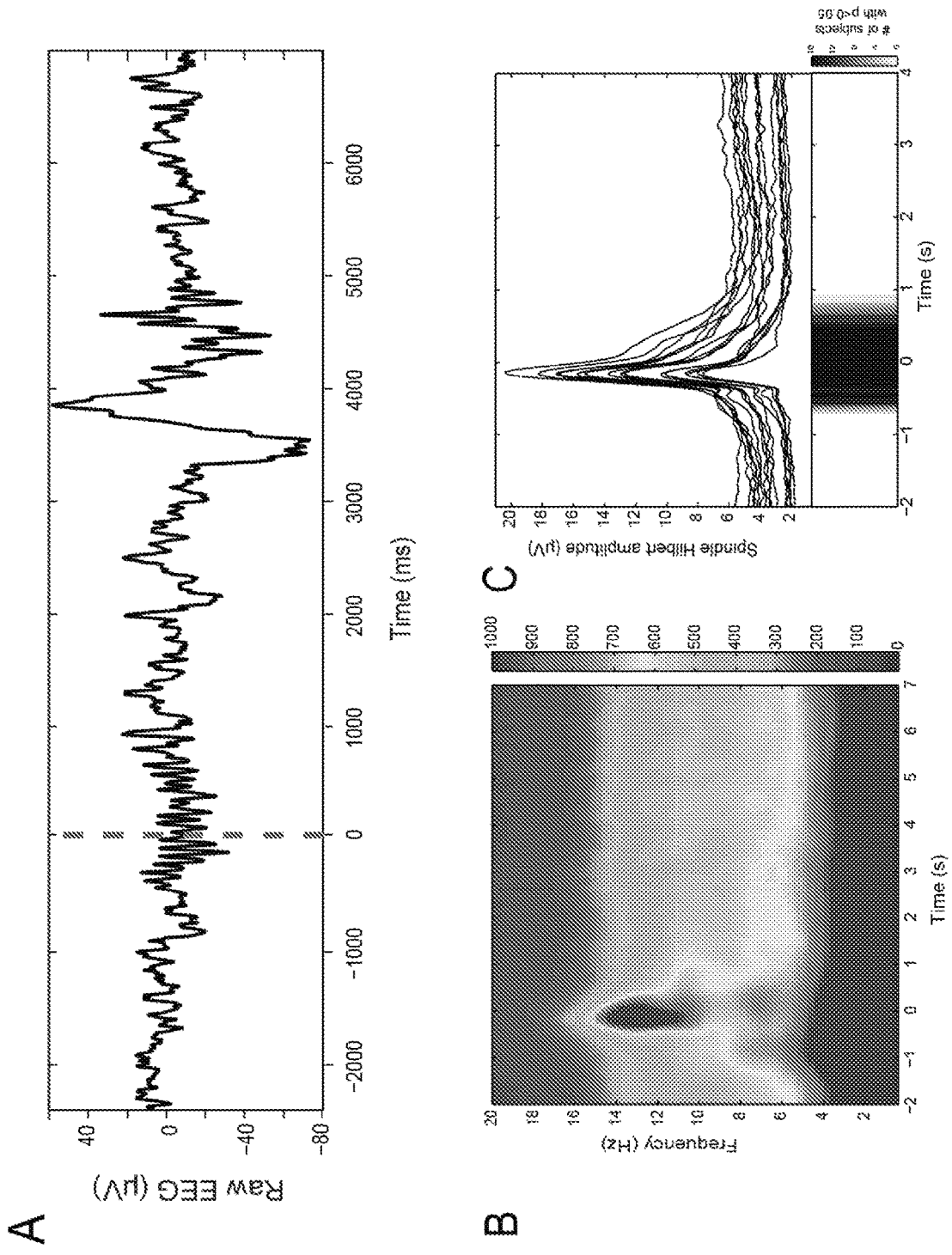
FIGS. 3A-3C show spindle FB-tACS only applies tACS when spindle activity (11-16 Hz) is prevailing in the EEG. (A) Single EEG trace of a representative participant with a detected spindle (pink dashed line) using our online spindle detection algorithm. Online spindle detection was used to control the stimulation start ensuring cortical stimulation exclusively during NREM spindles. Trace was obtained from a sham night (only triggering, no stimulation). (B) Spectrogram of Fz-CPz of a representative participant during sham night shows that tACS triggers were present during sleep spindles as indicated by increased spindle activity (10-16 Hz) around 0 (represents onset of tACS for verum condition). (C) Spindle (11-16 Hz) Hilbert amplitude averaged spindle triggers of Fz-CPz during sham night. Each line represents a participant (n=16). Lower panel illustrates within-subject statistics. An unpaired one-sided t-test (right-tailed) was performed for the spindle Hilbert amplitude at each time-point of the illustrated epoch to the overall mean of the epoch (−2.5 to 7.5 s around trigger) for all correct NREM spindle triggers. Grey-black colored bars illustrate the number of participants showing significant increased spindle amplitude at the respective time-point compared to the mean of the whole epoch. Around 0 ms ("stimulation onset") all participant showed significantly increased, prevailing spindle activity compared to the rest of the epoch.

TACS was Restricted to NREM Episodes with Prevailing Sleep Spindle Activity:

The spindle detection algorithm led to tACS application solely when sleep spindle activity was prevailing as illustrated in FIGS. 3A-3C. In all participants spindle activity was significantly higher at and around the algorithm spindle detection time-point ("stimulation onset") compared to the rest of the epoch as verified by the Hilbert amplitude between 11-16 Hz during the sham nights (FIG. 3C). Furthermore, combining the NREM and sigma threshold detection allowed for a successful identification of prevailing spindle activity during NREM sleep with a negligibly low number of stimulations during REM or wakefulness (FIGS. 2A-2E and Table 2).

TABLE 2

Number of spindle detections per sleep stage (n = 15)

| | SHAM Mean (SEM) | VERUM Mean (SEM) | Statistics paired t-test (p) |
|---|---|---|---|
| Uncorrected | | | |
| Wake | 4.5 (1.0) | 6.2 (1.0) | >0.1 |
| NREM stage 1 | 2.2 (0.8) | 1.6 (0.3) | >0.1 |
| NREM stage 2 | 406.1 (44.7) | 433.5 (32.9) | >0.1 |
| NREM stage 3 | 254.0 (35.4) | 191.3 (37.4) | 0.02 |
| REM sleep | 1.4 (0.6) | 1.6 (0.7) | >0.1 |
| Corrected (included in analysis) | | | |
| NREM stage 2 | 382.4 (42.8) | 421.3 (32.5) | >0.1 |
| NREM stage 3 | 239.2 (35.4) | 182.3 (35.5) | 0.03 |

Figure 4A:
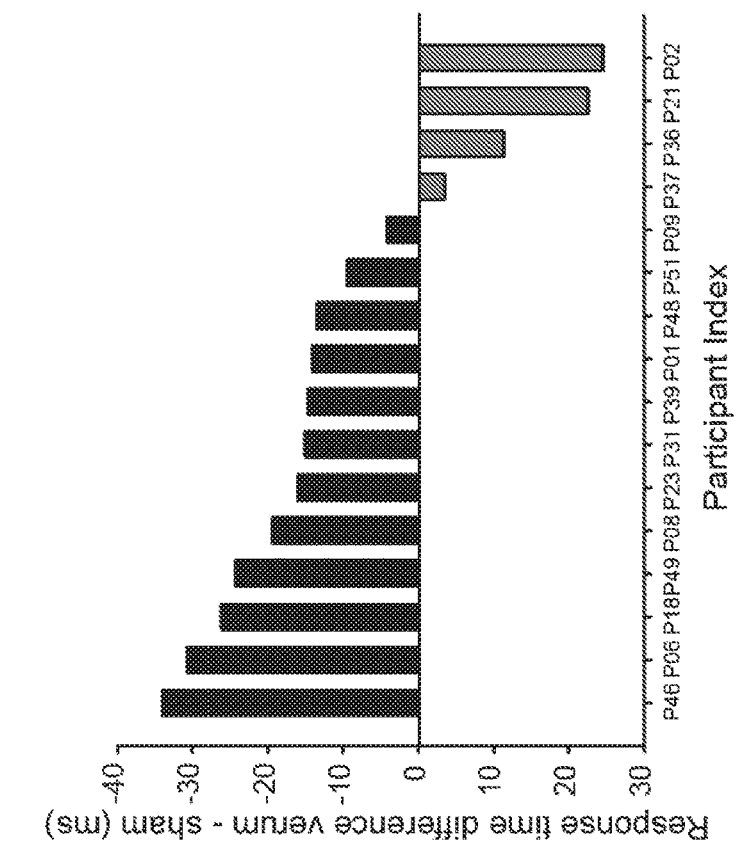
FIGS. 4A-4B show spindle FB-tACS increases motor sequence tapping speed (response time). (A) Spindle FB-tACS caused superior speed improvement (reduction in response time) compared to a night with sham condition as verified with a robust linear mixed model analysis (* n=16, $F(1,11.8)=5.7$, $p=0.035$). Bars illustrate mean+s.e.m. B) Difference of overnight speed gain (verum−sham) for each individual. Black bars illustrate participants with superior overnight speed gain during verum compared to sham (responders, n=12) and grey bars indicate participants with inferior overnight speed gain during verum compared to sham (non-responders, n=4).

Spindle FB-tACS Improved Motor Memory Consolidation:

Superior motor memory consolidation was found (absolute overnight difference, FIG. 4A) assessed by speed for correct trials (reduction in response time, a measure for the tapping time between key presses) after spindle FB-tACS (−21.01±5.72 ms) compared to sham (−10.97±7.69 ms; robust linear mixed model factor condition: $F(1,11.8)=5.7$, p=0.035). 12 of 16 participants (responders) showed this beneficial effect of spindle FB-tACS on motor memory 10.9)=5.17, p=0.04) further confirming that specifically speed was significantly modulated by FB-tACS.

TABLE 3

PVT and questionnaire results (n = 16)

Figure 4B:
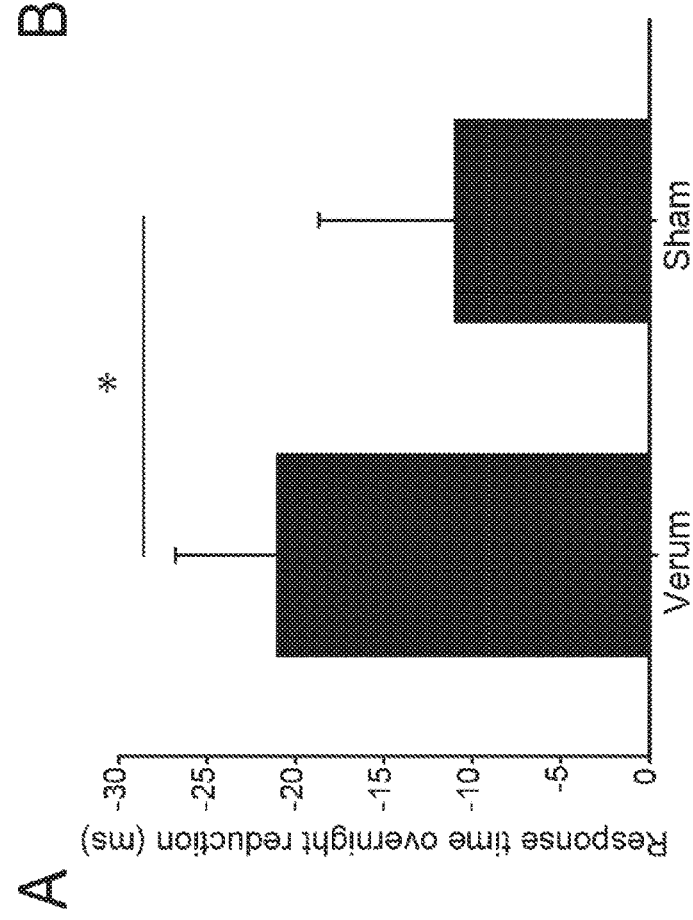
Figure 5A:
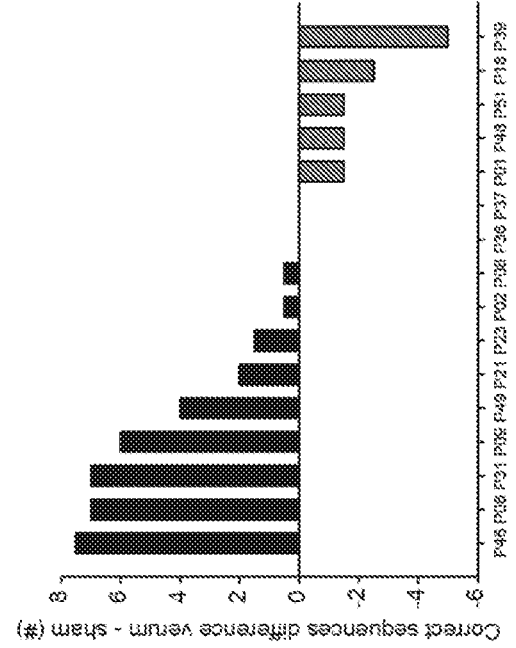
FIGS. 5A-5D show the effect of spindle FB-tACS on motor sequence tapping accuracy. Spindle FB-tACS had no significant effect on (A) number of correct tapped sequences or (C) number of errors compared to a sham night as verified with a robust linear mixed model analysis (n=16, factor condition: correct sequences $F(1,11.8)=1.28$, $p=0.28$; errors: $F(1,11.8)=0.12$, $p=0.73$). (B) and (D) illustrate difference (verum−sham) in number of correct trials and errors for each individual, respectively. Black bars illustrate participants with superior performance gain during verum compared to sham and grey bars participants with inferior overnight speed gain during verum compared to sham.
Figure 5B:
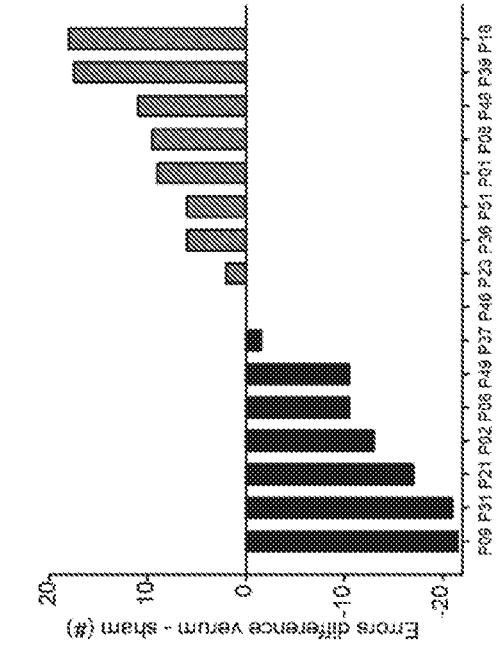
Figure 5C:
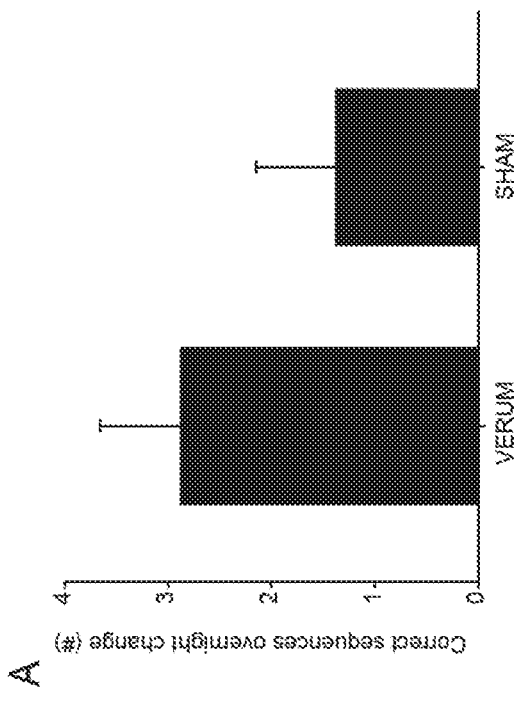
Figure 5D:
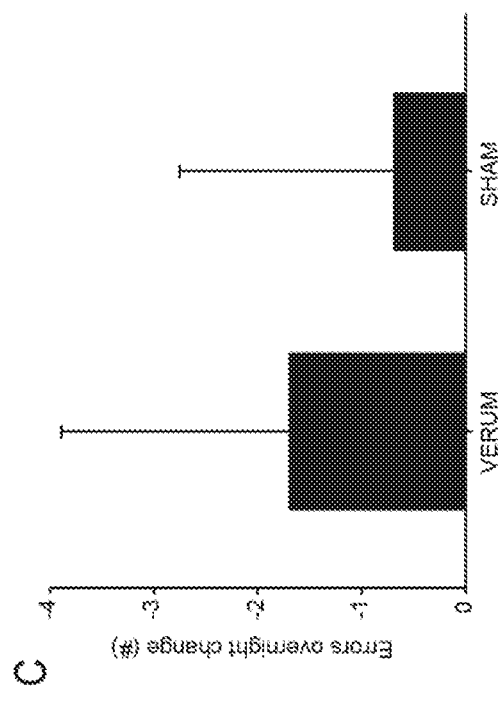

|  | SHAM Mean (SEM) | VERUM Mean (SEM) | Statistics Factor Condition (p) | Interaction Condition × Session (p) |
|---|---|---|---|---|
| PVT (ms) |  |  |  |  |
| Mean RT difference | −6.2 (6.4) | 1.5 (4.4) | >0.1 | >0.1 |
| Mean RT evening | 257.4 (6.3) | 249.2 (6.2) | >0.1 | >0.1 |
| Mean RT morning | 251.2 (4.5) | 250.7 (4.6) | >0.1 | >0.1 |
| Subjective alertness (VAS) |  |  |  |  |
| Sleepiness difference | 1.0 (0.5) | 0.6 (0.7) | >0.1 | >0.1 |
| Sleepiness evening | 5.1 (0.4) | 5.2 (0.6) | >0.1 | >0.1 |
| Sleepiness morning | 6.1 (0.5) | 5.8 (0.4) | >0.1 | >0.1 |
| Concentration difference | −0.3 (0.4) | −0.7 (0.4) | >0.1 | >0.1 |
| Concentration evening | 6.8 (0.4) | 6.9 (0.5) | >0.1 | >0.1 |
| Concentration morning | 6.4 (0.5) | 6.2 (0.5) | >0.1 | >0.1 |
| Motivation difference | −0.1 (0.3) | −0.4 (0.4) | >0.1 | >0.1 |
| Motivation evening | 6.9 (0.5) | 7.0 (0.5) | >0.1 | >0.1 |
| Motivation morning | 6.8 (0.4) | 6.5 (0.5) | >0.1 | >0.1 |
| Subjective sleep quality (VAS) |  |  |  |  |
| How quiet was your sleep? | 5.4 (0.5) | 5.0 (0.4) | >0.1 | >0.1 |
| How deep did you sleep? | 5.5 (0.6) | 5.4 (0.5) | >0.1 | >0.05 | consolidation (FIG. 4B). This effect was not driven by baseline performance differences since the response time in the evening was not different between sham and verum conditions (factor condition: F(1,11.8)=0.0, p=0.97). Furthermore, the reported motor sequence speed gains cannot simply be explained by an improvement in attentional reaction time, as performance in a psychomotor vigilance task was not significantly affected by stimulation (Table 3). Number of errors and number of correctly tapped sequences were not affected by stimulation (FIGS. 5A-5D; all p for factor condition >0.1). Number of correctly tapped sequences has previously been used as a measure for speed (Marshall et al., *Nature* 444:610 (2006); Rasch et al., *Nat. Neurosci.* 12:396 (2009); Walker et al., *Neuron* 35:205 (2002)). However, this measure likely assesses both accuracy and speed, because it is dependent on number of errors (accuracy) and response time (speed). Indeed, it was found that overnight changes in correctly tapped sequences was negatively correlated with number of errors (pooled data for both conditions, r(30)=−0.59, p<0.001). In addition, it was found that decreased response time (increase in speed) across the sleep period was related to an increase in the number of correctly tapped sequences (pooled data for both conditions, r(30)=−0.52, p<0.005). Of note, speed and accuracy were not significantly correlated and therefore represent two independent components (pooled data for both conditions, r(30)=−0.25, p>0.1). Thus, it is important to separate those two components of motor learning because they might be differentially affected by stimulation. Thus, stimulation effects might be masked if combination measures (e.g., number of correct sequences) are used. To confirm that the speed aspect of the number of correctly tapped sequences was also significantly affected by stimulation condition, the robust linear mixed model (dependent variable: number of correctly tapped sequences) was controlled for accuracy by including number of errors as a covariate. This corrected model indeed revealed a significant effect of stimulation condition on number of correctly tapped sequences (F(1, Spindle FB-tACS had no effect on declarative memory (difference in number of recalled word-pairs: sham: 8.00±1.23 words; verum: 7.94±1.07 words; F(1,11.8)=0.00, p=0.97). Collectively, spindle FB-tACS improved sleep-related gains in motor sequence tapping speed but had no influence on motor sequence accuracy or declarative memory.

Figures 7A, 7B:
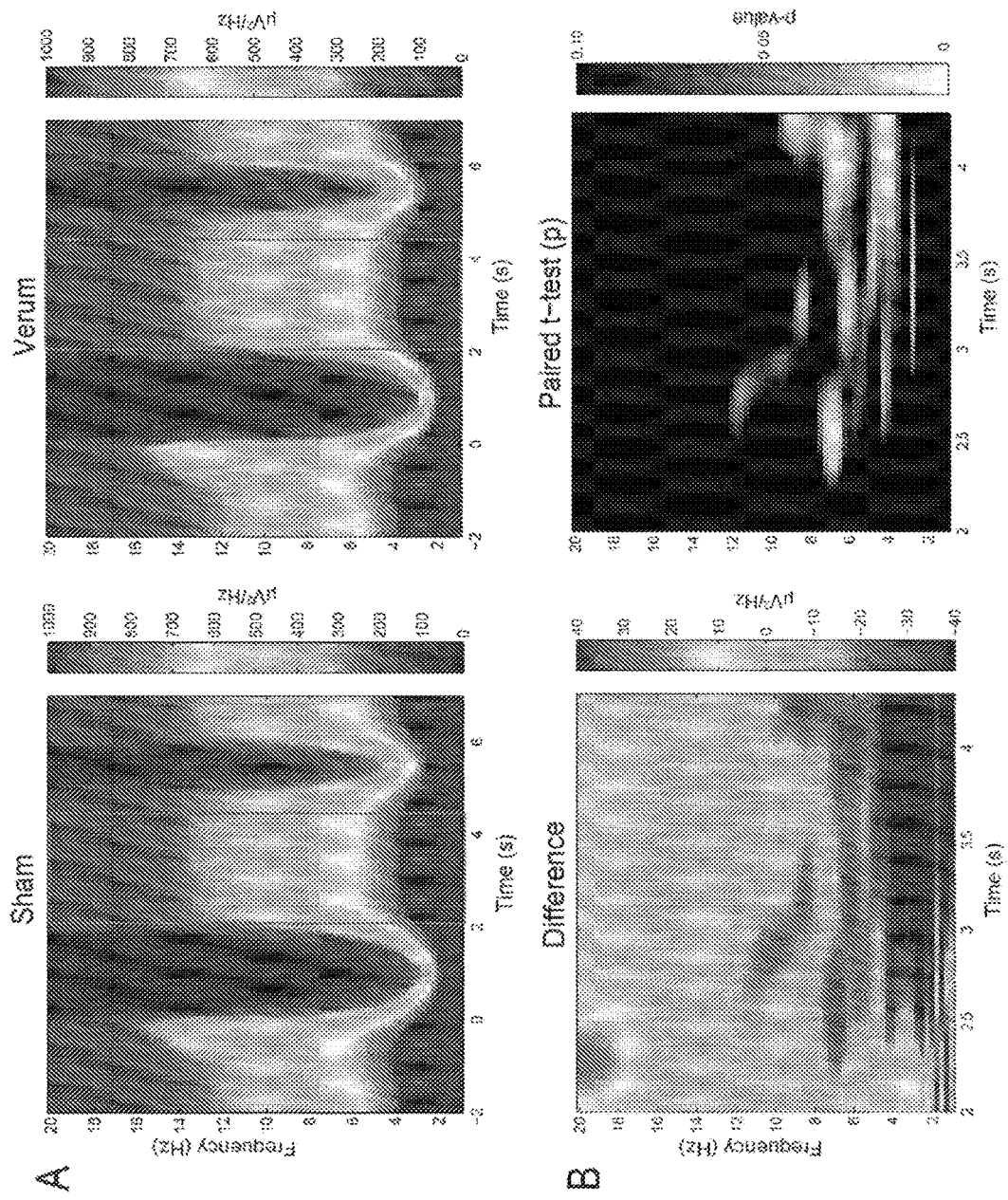
FIGS. 7A-7B show FB-tACS has no effect on spindle activity during NREM stage 3. (A) Time-frequency plots (n=15) of NREM stage 3 (N3) for each condition averaged for all channels. Timepoint 0 represents spindle detection (trigger). Power values between 0 and 2 s and 4.3 to 6 s are very low because of artifact blanking and linear interpolation. (B) Differences of spectrograms (verum−sham) for longest artifact free interval (pink window upper panel) and corresponding p-values of a paired t-test between sham and verum condition (p values>0.1 are black).

Spindle FB-tACS had No Effect on Sleep Architecture but Increased Post-Stimulation Spindle Activity:

Given this beneficial effect of FB-tACS on motor memory consolidation, it was next investigated whether FB-tACS enhanced sleep spindle activity. It was hypothesized that a selective enhancement of spindle activity by stimulation was the underlying mechanism of this memory improvement. The possibility that overall effects on the macroscopic structure of sleep could account for the effect on memory was first excluded. None of the time spent in individual sleep stages or total sleep time were significantly different between the sham and verum conditions (Table 4, all p of factor condition >0.1). Due to the pronounced stimulation artifact, analysis was only possible in a stimulation free interval. Thus, it was then examined how short epochs of 12 Hz-tACS affected the NREM sleep EEG in a short stimulation-free interval after the tACS artifact compared to sham condition (only spindle detection trigger, no tACS applied). For this analysis, 15 out of 16 participants were included due to unusable EEG for one participant. The analysis was performed separately for NREM sleep stage 2 (N2) and 3 (N3) to account for number of included trials, light (N2) and deep sleep (N3), and different thalamic hyperpolarization levels. Spindle FB-tACS led to a broad increase in spindle activity around 11-16 Hz only in N2 averaged over all electrodes, with motor memory responders (n=11) showing an increase in very fast spindle frequencies (15-16 Hz) compared to non-responders (n=4, show decrease; FIGS. 6A-6C). Besides a selective increase in spindle activity, the stimulation also significantly reduced power in the delta and theta range in N2 (FIGS. 6A-6C) and N3 (FIGS. 7A-7C).

Figures 8A, 8B, 8C:
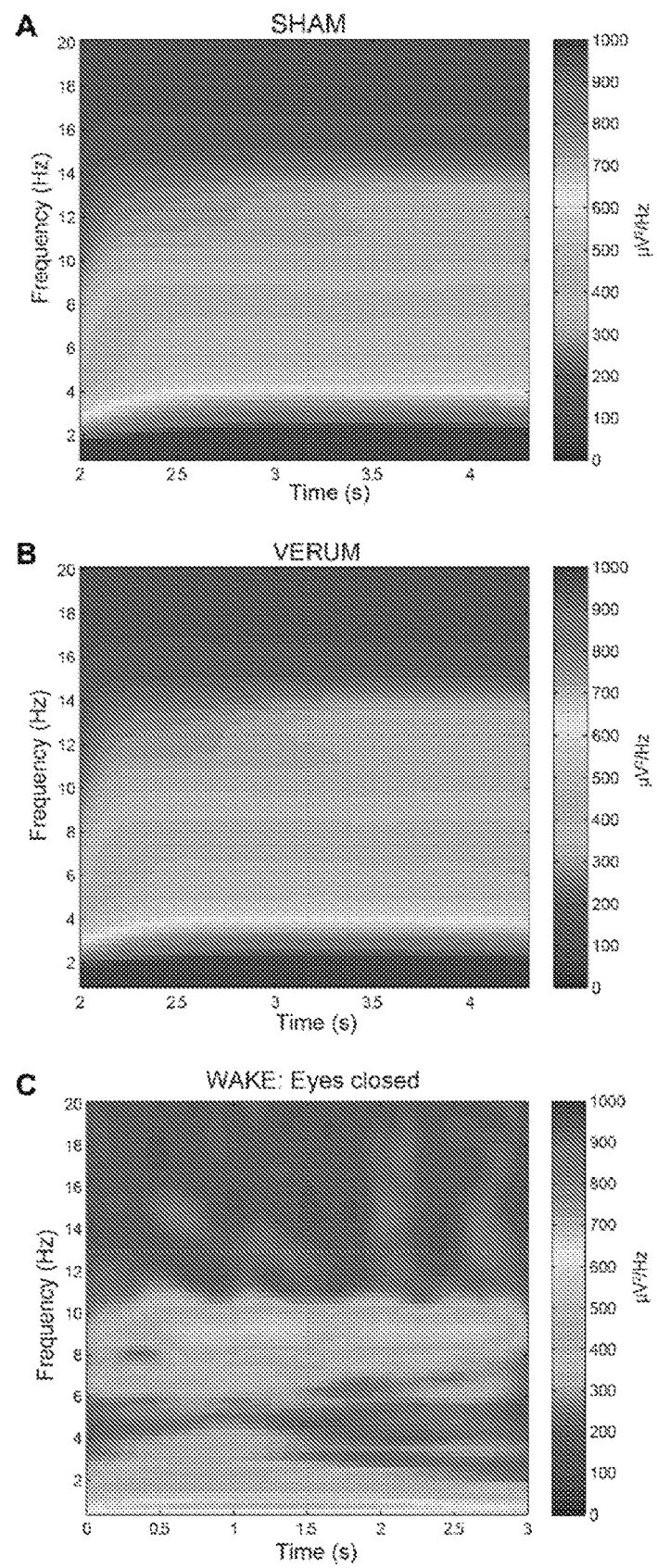
FIGS. 8A-8C show FB-tACS post-stimulation period and spindle activity increase do not resemble arousal periods. Time-frequency plots (n=15) of NREM stage 2 (N3) for sham (A) and verum (B) averaged for all channels during post spindle detection/tACS interval. (C) Time-frequency plot of averaged 3 s windows of eyes closed condition for a representative subject (occipital electrode which shows strongest alpha modulation during wakefulness).

Since sigma activity overlaps with alpha activity during wakefulness one might argue that the stimulation leads to arousal that could explain an increase in sigma activity. However, the results clearly show that this is not the case: (1) wakefulness alpha is between 8-12 Hz whereas the increase in spindle activity is between 12-16 Hz (FIGS. 8A-8C); (2) The spectrogram after the stimulation has a similar profile for sham and verum epochs, looking clearly different from a typical wakefulness (eyes closed) period; and (3) number of wakefulness periods and perceived sleep depth were not significantly different between conditions (Table 3 and Table 4).

TABLE 4

Sleep architecture comparison between sham and verum condition (n = 16)

|  | Sham Mean (SEM) | Verum Mean (SEM) | Statistics Factor Condition (p) | Interaction Condition × Session (p) |
| --- | --- | --- | --- | --- |
| Total sleep time (min) | 447.0 (4.5) | 447.6 (4.1) | >0.1 | >0.1 |
| Sleep efficiency (%) | 93.1 (0.9) | 93.3 (0.9) | >0.1 | >0.1 |
| Sleep latency (min) | 10.6 (2.0) | 12.8 (3.2) | >0.1 | >0.1 |
| WASO (%) | 5.3 (0.8) | 4.6 (0.6) | >0.1 | >0.1 |
| Stage 1 (%) | 3.4 (0.6) | 3.1 (0.3) | >0.1 | >0.1 |
| Stage 2 (%) | 50.2 (1.7) | 49.9 (1.9) | >0.1 | >0.1 |
| Stage 3 (%) | 19.4 (1.7) | 18.7 (1.7) | >0.1 | >0.1 |
| NREM sleep (%) | 69.6 (1.3) | 68.6 (1.2) | >0.1 | >0.1 |
| REM sleep (%) | 20.1 (0.9) | 21.6 (0.9) | >0.1 | >0.1 |

FB-tACS Induced Enhancement of Spindle Activity Predicted Improvement in Motor Memory Consolidation:

In order for sleep spindle activity to promote motor memory speed gains, the stimulation-induced increase in spindle activity should be related to the improvement in motor memory consolidation. Given that non-responders and responders mainly differed in spindle activity increase for very fast frequencies (15-16 Hz) the correlation analysis was restricted to this frequency window. Indeed, a significant negative correlation was found between the verum-related change in response time and spindle activity for the very fast spindle frequency range indicating that the increase in fast sleep spindle activity predicted reduction in tapping time (increase in speed) due to verum stimulation (FIG. 6C). This negative correlation was found globally but only reached trend-level or significance for mainly parietal and occipital electrodes (Pearson correlation of merged parieto-occipital cluster (4 electrodes): r(13)=−0.65, p=0.009, cluster survives supra-threshold cluster analysis).

Figures 9A, 9B:
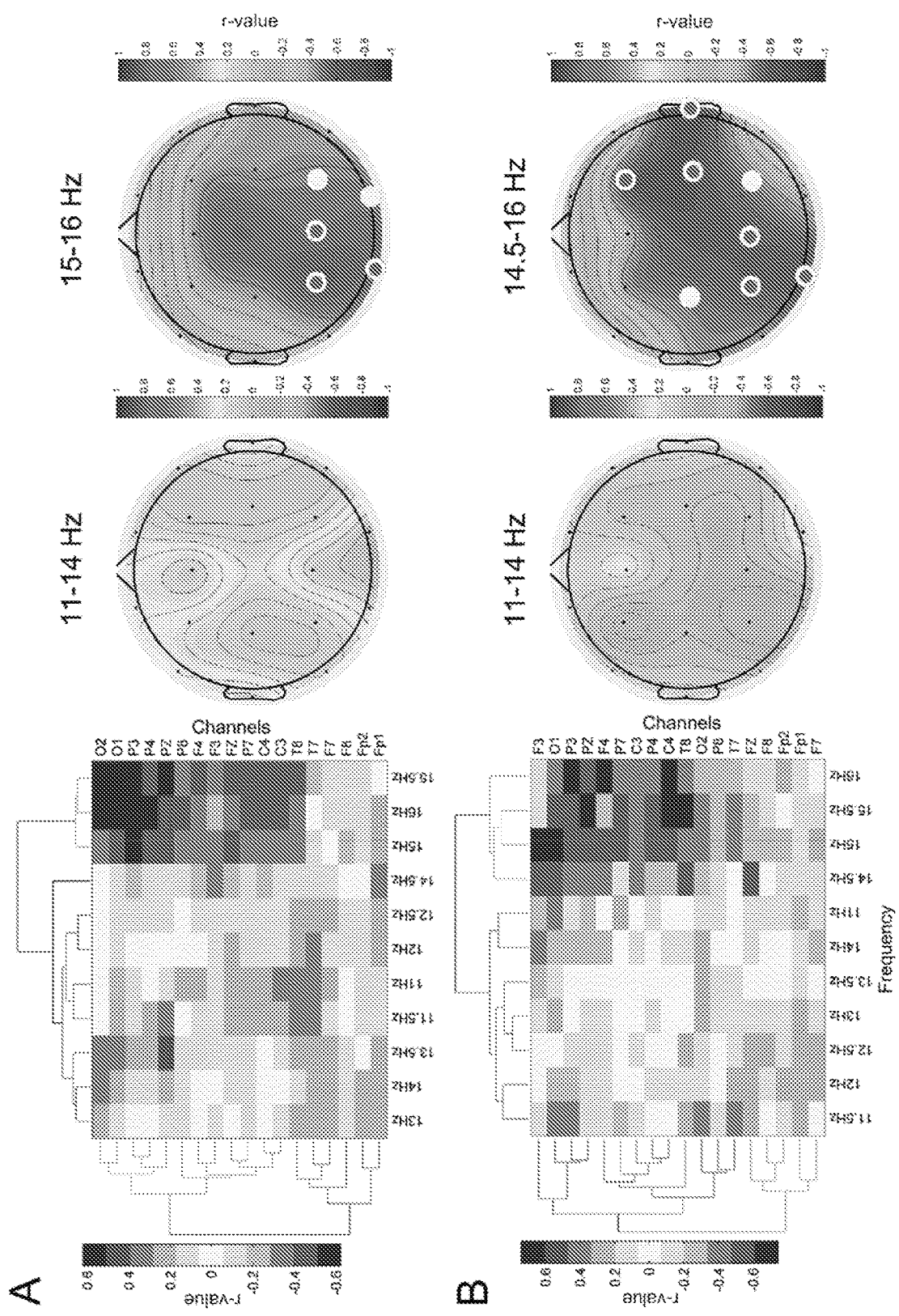
FIGS. 9A-9B show the relationship between sleep-dependent motor memory consolidation and spindle characteristics in absence of stimulation. Two dimensional hierarchical cluster trees (dendrogram) and heat plots of the r-values of the correlation between sleep-dependent reduction in response time (speed gain) during the sham night and (A) spindle density, and (B) spindle duration. Colored branches illustrate clusters with an Euclidean distance below 1.3. Negative correlation coefficients show that more pronounced appearance of the respective spindle characteristic was reflected in sleep-dependent response time decrease (speed increase). Right column illustrates corresponding correlation coefficient (r) topographical plots of clustered frequency bands (based on clustering in dendrogram). Electrodes (black dots) that showed significant correlations (Pearson correlation) are marked with grey dots ($p<0.05$) and electrodes that showed a trend-level with white dots (n=16, $p\geq 0.05$ and $p<0.1$). The size of the cluster in A (6 neighboring electrodes with grey and white dots) was trend-level after performing a supra-threshold cluster analysis, the cluster in B (8 neighboring electrodes) was significant.

Spindle Characteristics and Sleep-Dependent Motor Memory Consolidation are Similarly Correlated During the Sham Night:

To further confirm the role of fast sleep spindles in motor memory consolidation, it was finally examined whether a similar relationship exists between motor memory consolidation and different NREM sleep spindle characteristics (e.g., density) in the absence of stimulation (sham). Overnight change in response time was negatively correlated with spindle density and duration, again for the same frequency bins (15-16 Hz for density and 14.5-16 Hz for duration) and posterior electrodes (FIGS. 9A-9B). This finding convincingly confirms that characteristics of fast spindles, specifically density and duration, are important for sleep-dependent motor memory consolidation.

Discussion

A successful framework was established to investigate the functional role of specific transient brain oscillations in cognitive processes by applying targeted, individualized and feedback-controlled weak electrical brain stimulation. It was found that spindle FB-tACS can enhance sleep spindle activity in a broad frequency range during NREM stage 2 sleep without increasing other sleep rhythms or time spent in individual sleep stages. Furthermore, spindle FB-tACS enhanced motor sequence consolidation by means of increased speed, and fast sleep spindle activity played a functional role in this gain. This provides the first direct demonstration of the functional role of sleep spindle activity in motor memory consolidation.

Sleep spindles have previously been hypothesized to benefit memory formation (Rasch et al., *Physiol. Rev.* 93:681 (2013)). For instance, sleep-dependent improvements in declarative and procedural learning paradigms correlated with sleep spindle characteristics (Rasch et al., *Nat. Neurosci.* 12:396 (2009); Clemens et al., *Neuroscience* 132:529 (2005); Holz et al., *J. Sleep Res.* 21:612 (2012)). Furthermore, spindles were increased during sleep following the training of these learning paradigms compared to a control condition (Barakat et al., *Behav. Brain Res.* 217:117 (2011); Gais et al., *J. Neurosci.* 22:6830 (2002); Johnson et al., *Proc. Natl. Acad. Sci. USA* 109:18583 (2012); Schmidt et al., *J. Neurosci.* 26:8976 (2006)). In further support of a central role of sleep spindles in memory processes, patients with schizophrenia show a pronounced reduction in sleep spindles that correlates with deficits in sleep-dependent motor memory consolidation (Manoach et al., *J. Psychiatr. Res.* 44:112 (2010); Wamsley et al., *Biol. Psychiatry* 71:154 (2012)). However, these studies were restricted to correlations leaving it unclear whether learning-associated changes in sleep spindle dynamics are an epiphenomenon or indeed play a functional role in memory consolidation. Previous attempts in manipulating sleep in humans (e.g., auditory stimulation, pharmacology or slow-oscillatory direct current stimulation) were only successful in enhancing sleep spindles as a side effect of enhancing slow oscillations (Del Felice et al., *Brain Stimulation* 8:567 (2015); Marshall et al., *Nature* 444:610 (2006); Ngo et al., *Neuron* 78:545 (2013); Westerberg et al., *Neurobiol. Aging* 36:2577 (2015)) or the time spent in sleep stages, such as slow wave sleep (Mednick et al., *J. Neurosci.* 33:4494 (2013)). In addition, tES approaches so far only enhanced declarative memory but failed to improve procedural tasks (Barham et al., *Neurosci, Biobehav, Rev,* 63:65 (2016)) even though one of the studies reported increases in sleep spindle measures along with enhanced slow oscillations/slow wave sleep (Marshall et al., *Nature* 444:610 (2006)). A possible explanation for this missing effect on procedural memory is that the reported significant increase in sleep spindles were only found for slow-frequency spindles but not for the fast spindles (Marshall et al., *Nature* 444:610 (2006)). In addition all studies using tES to modulate NREM sleep and enhance memory consolidation applied either slow-oscillatory tDCS/ACS (0.75 Hz) or tDCS (Barham et al., *Neurosci, Biobehav, Rev,* 63:65 (2016)) and were therefore not optimized to selectively target sleep spindles. This is the first demonstration of the ability to selectively enhance sleep spindle activity along with motor memory consolidation and therefore provide a functional role of these oscillations in cognitive processes.

Spindle FB-tACS specifically enhanced sleep-dependent speed gains and not accuracy in a motor sequence tapping paradigm reflected in a significant decrease of response time, but not error rate. This is in accordance with previous studies that mainly found a robust effect of sleep on speed measures, e.g., (Marshall et al., *Nature* 444:610 (2006); Mednick et al., *J. Neurosci.* 33:4494 (2013); Walker et al., *Neuron* 35:205 (2002); Nishida et al., *PLoS One* 2:e341 (2007); Brawn et al., *J. Neurosci.* 30:13977 (2010)). However, most of these studies used number of correct sequences per trial as a measure for speed. The present results revealed that the number of correct trials is not independent of the error rate and therefore relates to the accuracy of the performance. In addition, some studies also indicate a beneficial effect of sleep on the error rate (accuracy) (Walker et al., *Learn. Mem.* 10:275 (2003)). In other words, changes/variations in error rate might be reflected in the number of correct sequences and could therefore mask/confound sleep and intervention condition effects on speed measures. By including error rate as a covariate in the present model, stimulation condition had a significant effect on number of correctly tapped sequences, showing that spindle FB-tACS selectively enhanced sleep-dependent speed benefits but not accuracy. Collectively, these findings argue for the use of more "pure" measures of speed in motor sequence tapping tasks, e.g., by focusing on the response time of correctly tapped sequences or controlling for the error rate in future models.

The stimulation-induced overnight gains in motor sequence learning were mediated by the fast sleep spindle activity which is in line with previous literature showing a correlation of motor memory exclusively with fast spindle characteristics (Barakat et al., *Behav. Brain Res.* 217:117 (2011)). The present studies replicate this correlation in the sham night with different spindle characteristics and found the same frequency bins and electrodes of spindle density and duration significantly correlating with motor memory consolidation. Several studies hypothesized that slow and fast frequency spindles might serve different functions (De Gennaro et al., *Sleep Med. Rev.* 7:423 (2003); Barakat et al., *Behav. Brain Res.* 217:117 (2011); Lustenberger et al., *Sleep* 38:1093 (2015)). Each spindle type shows a different topography with slower spindle frequencies (around 12 Hz) being preferentially visible over frontal areas whereas fast sleep spindles (around 14 Hz) are more pronounced over centro-parietal regions (De Gennaro et al., *Sleep Med. Rev.* 7:423 (2003); Andrillon et al., *J. Neurosci.* 31:17821 (2011); De Gennaro et al., *Sleep Res. Online* 3:155 (2000); Jobert et al., *Neuropsychobiology* 26:210 (1992)). Considering that the present correlations with motor memory consolidation were restricted to the fast spindle frequency range, these results underline the assumption that slow and fast sleep spindles might serve different functions. Therefore, the present results highlight the importance of separating slow and fast frequencies for future analyses of sleep spindles.

Besides sleep spindles, slow waves have been proposed to play an important role in memory consolidation (Rasch et al., *Physiol. Rev.* 93:681 (2013)). However, a superior sleep-dependent speed gain for verum condition was found despite a spindle FB-tACS induced decrease in delta and theta power, pointing to a limited role of slow waves in this specific process. Along this line, some studies have suggested a role of spindles in motor memory consolidation in dissociation from effects mediated by the slow waves. Using tones to reduce slow waves and REM sleep without changing sleep spindles, Genzel et al., *Sleep* 32:302 (2009) were able to preserve the consolidation of procedural and declarative memory. Enhancing slow wave activity (SWA, 0.5-4 Hz) but decreasing spindle activity using the GABA reuptake inhibitor Tiagabine led to diminished memory consolidation in a motor sequence tapping task (Feld et al., *Sleep* 36:1317 (2013)). Finally, patients with schizophrenia who show reduced motor sequence consolidation also exhibit a pronounced decrease in sleep spindles with negligible changes in slow wave activity (Ferrarelli et al., *Am. J. Psychiatry* 167:1339 (2010); Manoach et al., *J. Psychiatr. Res.* 44:112 (2010); Wamsley et al., *Biol. Psychiatry* 71:154 (2012); Seeck-Hirschner et al., *J. Psychiatr. Res.* 44:42 (2010)). Here, it is shown that selective spindle enhancement had no effect on declarative memory consolidation despite this hypothesis from previous studies (Rasch et al., *Physiol. Rev.* 93:681 (2013)). A possible explanation for this missing effect could be the reduction in delta activity because sleep spindles might only be beneficial for this memory type in combination with slow waves (Molle et al., *Prog. Brain Res.* 193:93 (2011)).

The present results further suggest that sleep spindles and slow waves cannot be independently modulated. Along this line, previous studies have shown that specific sleep spindle characteristics and slow waves are inversely related (De Gennaro et al., *Sleep Med. Rev.* 7:423 (2003); Andrillon et al., *J. Neurosci.* 31:17821 (2011); Himanen et al., *J. Sleep Res.* 11:35 (2002); Steriade et al., *Sleep Res. Online* 1:1 (1998); Dijk et al., *Brain Res.* 626:190 (1993); Uchida et al., *Brain Res. Bull.* 27:93 (1991)). For instance, spindle density and spindle frequency are reduced in early NREM sleep, in the middle of NREM cycles and N3 when SWA is maximal (Andrillon et al., *J Neurosci.* 31:17821 (2011)). Further studies underlining this notion found less spindle activity in the recovery night after sleep deprivation that is marked by increased SWA (De Gennaro et al., *Sleep Med. Rev.* 7:423 (2003); Dijk et al., *Brain Res.* 626:190 (1993)) or reported negative correlations between spindle measures (e.g., sigma activity) and SWA during NREM sleep (Uchida et al., *Brain Res. Bull.* 27:93 (1991); Aeschbach et al., *J. Sleep Res.* 2:70 (1993)). The present results further support and extend the notion that SWA and sleep spindles share a reciprocal relationship.

Collectively, spindle FB-tACS revealed the functional relationship between fast sleep spindles and motor memory consolidation and has thus promise as a potential therapeutic for treating motor memory impairments afflicting patients with psychiatric and neurological disorders (Manoach et al., *J. Psychiatr. Res.* 44:112 (2010); Wamsley et al., *Biol. Psychiatry* 71:154 (2012); Seeck-Hirschner et al., *J Psychiatr. Res.* 44:42 (2010)) and older individuals (Fogel et al., *Hum. Brain Mapp.* 35:3625 (2014)). In a broader context, the present results provide convincing evidence that targeted and individualized stimulation approaches are fundamental for selectively boosting transient brain oscillations. Furthermore, this study provides a model paradigm for establishing the functional role of transient brain oscillations in human behavior. The present FB-tACS design is a radical departure from the former stimulation approach because it takes individual, endogenous network activity into account. Stimulation success likely depends on the underlying network activity as has been convincingly shown in in-vivo, in-vitro and computational studies (Schmidt et al., *Brain Stimul.* 7:878 (2014); Ali et al., *J. Neurosci.* 33:11262 (2013); Fröhlich et al., *Neuron* 67:129 (2010); Ozen et al., *J. Neurosci.* 30:11476 (2010); Reato et al., *PLoS Comput. Biol.* 9:e1002898 (2013)). This is why feedback-controlled approaches provide a promising starting point for individualized treatment paradigms that successfully target pathological network dynamics with non-invasive brain stimulation.

The foregoing is illustrative of the present invention, and is not to be construed as limiting thereof. The invention is defined by the following claims, with equivalents of the claims to be included herein.

That which is claimed:

1. A method of improving memory or cognitive function in a subject, the method comprising:
   a) detecting a burst of oscillatory brain activity in the subject, wherein the detecting comprises identifying one or more sleep spindles; and
   b) passing an oscillating current through a skull of the subject in response to the detected burst of oscillatory brain activity, thereby improving memory or cognitive function in the subject relative to memory or cognitive function in an absence of the method, wherein the oscillating current is transcranial alternating current stimulation (tACS) at a frequency of 11-16 Hz that is frequency matched to the one or more sleep spindles in the detected burst of oscillatory brain activity.

2. The method of claim 1, wherein the burst of oscillatory brain activity is detected in a brain region comprising a thalamus and the oscillating current is passed through the skull of the subject into the same brain region.

3. The method, of claim 1, wherein the burst of oscillatory brain activity is detected in a first brain region comprising a thalamus and the oscillating current is passed through the skull of the subject into a second brain region different from the first brain region.

4. The method of claim 1, wherein the oscillating current is passed through the skull of the subject in an interval between bursts of oscillatory brain activity.

5. The method of claim 1, wherein the oscillating current is passed through the skull of the subject at random time points with respect to bursts of oscillatory brain activity.

6. The method of claim 1, wherein detecting the burst of oscillatory brain activity in the subject comprises identifying the one or more sleep spindles in real-time.

7. The method of claim 6, wherein identifying the one or more sleep spindles comprises:
   a) recording electroencephalograph (EEG) signals of the subject; and
   b) filtering and processing the EEG signals to identify the one or more sleep spindles.

8. The method of claim 7, wherein identifying the one or more sleep spindles further comprises:
   a) determining an occurrence of rapid eye movement (REM) versus non-REM sleep in the subject; and
   b) the filtering and processing of the EEG signals comprises band-pass filtering the EEG signals and applying a threshold to the band-pass-filtered EEG signals.

9. The method of claim 8, wherein a recording period is assigned to the non-REM sleep if:
   a) a 20 second moving-average wake index is below an awake index threshold; and
   b) a 20 second moving average REM index is below a REM index threshold.

10. The method of claim 9, wherein the awake index threshold and the REM index threshold are determined from a previous EEG recording of the subject.

11. The method of claim 9, wherein the awake index threshold is calculated using the formula:

$$\text{Log}(\text{AlphaPower} \times \text{MuscleArtifact}/\text{FastDeltaPower})$$

wherein:
AlphaPower is a power from the band-pass-filtered EEG signals with passband 8-12 Hz;
MuscleArtifact is a power from the band-pass-filtered EEG signals with passband 20-30 Hz; and
FastDeltaPower is a power from the band-pass-filtered EEG signals with passband 2-4 Hz;
wherein the powers are determined from 20 second windows.

12. The method of claim 9, wherein the REM index threshold is calculated using the formula $$\text{Log}(\text{BetaPower}/\text{DeltaPower})$$

wherein:
BetaPower is a power from the band-pass-filtered EEG signals with passband 18-40 Hz; and
DeltaPower is a power from the band-pass-filtered EEG signals with passband 0.5-4 Hz;
wherein the powers are determined from 20 second windows.

13. The method of claim 9, wherein identifying the one or more sleep spindles comprises:
   a) determining a presence of non-REM sleep; and
   b) determining a sigma power above a sigma threshold based on the EEG signals for 200 msec.

14. The method of claim 13, wherein the sigma threshold is calculated using the formula $$\text{mean sigma power} \times \text{sigma coefficient}$$

wherein:
mean sigma power is a power from the band-pass-filtered EEG signals with passband 11-16 Hz; and
sigma coefficient is determined from a previous recording of the subject and is chosen to maximize detection events corresponding to true spindles and minimize both false positives and false negatives.

15. The method of claim 6, wherein identifying the one or more sleep spindles comprises recording electrocorticogram signals, auditory signals, visual signals, and/or somatosensory input signals.

16. The method of claim 1, wherein passing an oscillating current through the skull of the subject comprises real-time application of the transcranial alternating current stimulation (tACS).

17. The method of claim 16, wherein the tACS is applied through a voltage-controlled current source.

18. The method of claim 16, wherein the tACS is applied through a set of scalp electrodes.

19. The method of claim 1, wherein auditory, visual, or somatosensory input is applied to the subject in addition to passing the oscillating current through the skull of the subject.

20. The method of claim 1, wherein the burst of oscillatory brain activity is detected in a thalamus of the subject.

21. The method of claim 1, wherein there is an increase in activity for spindle frequencies of 15-16 Hz based on the passed oscillating current.

22. A method of modulating or enhancing a frequency of occurrence, structure, amplitude, and/or synchronization of sleep spindles in a subject, the method comprising:
   a) detecting sleep spindles in the subject; and
   b) passing an oscillating current through a skull of the subject responsive to the detected sleep spindles, thereby modulating or enhancing the frequency of occurrence, structure, amplitude, and/or synchronization of additional sleep spindles in the subject relative to the frequency of occurrence, structure, amplitude, and/or synchronization of additional sleep spindles in an absence of the method, wherein the oscillating current is transcranial alternating current stimulation (tACS) at a frequency of 11-16 Hz to the detected sleep spindles.

23. The method of claim 22, wherein the sleep spindles are fast sleep spindles, and the tACS has a frequency of 15-16 Hz.

24. The method of claim 22, wherein there is an increase in activity for spindle frequencies of 15-16 Hz based on the passed oscillating current.

25. A method of treating a subject with a psychiatric or neurological symptom associated with impairment of sleep spindle oscillation and/or impairment of cognitive function, the method comprising:
  detecting sleep spindles in the subject; and
  passing an oscillating current through a skull of the subject responsive to the detected sleep spindles, thereby treating the psychiatric or neurological symptom associated with sleep spindles in the subject, wherein the oscillating current is transcranial alternating current stimulation (tACS) at a frequency of 11-16 Hz to the detected sleep spindles.

26. The method of claim 25, wherein the sleep spindles are fast sleep spindles, and the tACS has a frequency of 15-16 Hz.

27. The method of claim 25, wherein there is an increase in activity for spindle frequencies of 15-16 Hz based on the passed oscillating current.

* * * * *